(12) United States Patent
Stahmann et al.

(10) Patent No.: US 10,617,873 B2
(45) Date of Patent: Apr. 14, 2020

(54) COMMUNICATION OF THERAPY ACTIVITY OF A FIRST IMPLANTABLE MEDICAL DEVICE TO ANOTHER IMPLANTABLE MEDICAL DEVICE

(71) Applicant: Cardiac Packemakers, Inc., St. Paul, MN (US)

(72) Inventors: Jeffrey E. Stahmann, Ramsey, MN (US); William J. Linder, Golden Valley, MN (US); Howard D. Simms, Jr., Shoreview, MN (US); Keith R. Maile, New Brighton, MN (US); Michael J. Kane, Roseville, MN (US)

(73) Assignee: Cardiac Packemakers, Inc., St. Paul, MN (US)

( * ) Notice: Subject to any disclaimer, the term of this patent is extended or adjusted under 35 U.S.C. 154(b) by 243 days.

(21) Appl. No.: 14/592,671

(22) Filed: Jan. 8, 2015

(65) Prior Publication Data

US 2015/0196757 A1 Jul. 16, 2015

Related U.S. Application Data

(60) Provisional application No. 61/926,090, filed on Jan. 10, 2014.

(51) Int. Cl.
*A61N 1/362* (2006.01)
*H04B 13/00* (2006.01)
(Continued)

(52) U.S. Cl.
CPC .......... *A61N 1/3622* (2013.01); *A61B 5/0464* (2013.01); *A61B 5/4836* (2013.01);
(Continued)

(58) Field of Classification Search
CPC .................................................. A61N 1/3962
See application file for complete search history.

(56) References Cited

U.S. PATENT DOCUMENTS 4,787,389 A 11/1988 Tarjan
5,814,089 A * 9/1998 Stokes ................ A61N 1/3787
607/32
(Continued)

FOREIGN PATENT DOCUMENTS

WO 2006124833 A2 11/2006

*Primary Examiner* — Carl H Layno
*Assistant Examiner* — Jennifer L Ghand
(74) *Attorney, Agent, or Firm* — Seager, Tufte & Wickhem LLP

(57) ABSTRACT

Cardiac activity of the heart can be sensed using, for example, one or more leadless cardiac pacemakers (LCPs) that are implanted in a close proximity to the heart. Sensing cardiac activity by the one or more leadless cardiac pacemakers (LCPs) can help the system in determining an occurrence of cardiac arrhythmia. For treatment purposes, electrical stimulation therapy, for example anti-tachyarrhythmia pacing (ATP) therapy, can be delivered by at least one of the devices of the system. Such therapy can help treat the detected cardiac arrhythmia. In some instances, one of the leadless cardiac pacemakers can instruct one or more of the other devices to assist in providing pacing therapy. In some instances, one of the leadless cardiac pacemakers can instruct one or more of the other devices to temporarily stop providing therapy or to simply shut down while another device provides therapy.

8 Claims, 13 Drawing Sheets

(51) Int. Cl.
    *A61B 5/0464*     (2006.01)
    *A61B 5/00*     (2006.01)
    *A61N 1/36*     (2006.01)
    *A61N 1/372*     (2006.01)
    *A61B 5/0205*     (2006.01)
    *A61N 1/375*     (2006.01)
    *A61N 1/39*     (2006.01)

(52) U.S. Cl.
    CPC ...... *A61N 1/36114* (2013.01); *A61N 1/37288* (2013.01); *H04B 13/005* (2013.01); *A61B 5/0205* (2013.01); *A61N 1/3756* (2013.01); *A61N 1/37205* (2013.01); *A61N 1/3962* (2013.01)

(56) References Cited

U.S. PATENT DOCUMENTS

| | | | |
|---|---|---|---|
| 7,536,224 | B2 | 5/2009 | Ritscher et al. |
| 7,634,313 | B1 * | 12/2009 | Kroll .................. A61N 1/37288 607/2 |
| 8,457,742 | B2 | 6/2013 | Jacobson |
| 8,571,678 | B2 | 10/2013 | Wang |
| 8,744,572 | B1 | 6/2014 | Greenhut et al. |
| 2004/0147973 | A1 | 7/2004 | Hauser |
| 2006/0135877 | A1 * | 6/2006 | Giftakis ............... A61B 5/0402 600/513 |
| 2006/0135999 | A1 * | 6/2006 | Bodner .................. A61N 1/056 607/4 |
| 2007/0088394 | A1 | 4/2007 | Jacobson |
| 2009/0018599 | A1 * | 1/2009 | Hastings ................ A61N 1/372 607/32 |
| 2013/0231710 | A1 | 9/2013 | Jacobson |
| 2014/0214104 | A1 | 7/2014 | Greenhut et al. |

* cited by examiner

COMMUNICATION OF THERAPY ACTIVITY OF A FIRST IMPLANTABLE MEDICAL DEVICE TO ANOTHER IMPLANTABLE MEDICAL DEVICE

CROSS-REFERENCES TO RELATED APPLICATIONS

This application claims the benefit of U.S. Provisional Application No. 61/926,090, filed Jan. 10, 2014, the complete disclosure of which is herein incorporated by reference.

TECHNICAL FIELD

The present disclosure generally relates to systems, devices, and methods for detecting and treating cardiac arrhythmias and, more specifically to multiple device systems, methods, and devices for detecting and treating cardiac arrhythmias and/or other conditions.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices.

SUMMARY

The present disclosure relates generally to systems and methods for coordinating detection and/or treatment of abnormal heart activity using multiple implanted devices within a patient. It is contemplated that the multiple implanted devices may include, for example, pacemakers, defibrillators, diagnostic devices, and/or any other suitable implantable devices, as desired.

In one example, cardiac activity of the heart can be sensed using one or more leadless cardiac pacemakers (LCPs) either alone or in combination with one or more other devices. The leadless cardiac pacemakers (LCPs) can be implanted in a close proximity of the heart, such as in or on the heart. Sensing cardiac activity by the one or more leadless cardiac pacemakers (LCPs) can help the system determine an occurrence of a cardiac arrhythmia. For treatment purposes, electrical stimulation therapy, for example anti-tachyarrhythmia pacing (ATP) therapy, can be delivered by at least one of the devices of the system, such as one or more of the leadless cardiac pacemakers (LCPs). Such therapy can help treat the detected cardiac arrhythmia. In some instances, one of the leadless cardiac pacemakers (LCPs) can instruct one or more of the other devices to assist in providing pacing therapy. The one or more other devices may include, for example, another leadless cardiac pacemakers (LCP), a subcutaneous cardioverter-defibrillators (S-ICD), an implantable cardiac pacemakers (ICP), an external cardioverter-defibrillators, a diagnostic only device (devices that may sense cardiac electrical signals and/or determine arrhythmias but do not deliver electrical stimulation therapies), a neural stimulation device, and/or any other suitable device. In some embodiments, one of the leadless cardiac pacemakers can instruct one or more of the other devices to temporarily stop providing therapy or to simply shut down while another device provides therapy, such as anti-tachyarrhythmia pacing (ATP) therapy.

In one example, a therapy may be delivered to the heart of the patient using a first one of a plurality of implantable medical devices. A message may be communicated from the first one of the plurality of implantable medical devices to at least a second one of the plurality of implantable medical devices before and/or during delivery of the therapy. In a more specific example, a method for delivering anti-tachycardia pacing therapy to a heart of a patient may include sensing one or more cardiac signals and determining to deliver an anti-tachycardia pacing therapy based, at least in part, on the one or more sensed cardiac signals. An anti-tachycardia pacing therapy may be delivered to the heart of the patient using a first implantable medical device such as a leadless cardiac pacemaker (LCP). A message may be communicated from the leadless cardiac pacemaker (LCP) to a second implantable medical device before and/or during delivery of the anti-tachycardia pacing therapy. The behavior of the second implantable medical device may be modified in response to receiving the message from the first implantable medical device. For example, the second implantable medical device may assist the first implantable medical device in delivering the anti-tachycardia pacing therapy, temporarily stop providing therapy, temporary shutdown, or operate in any other suitable manner as desired.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
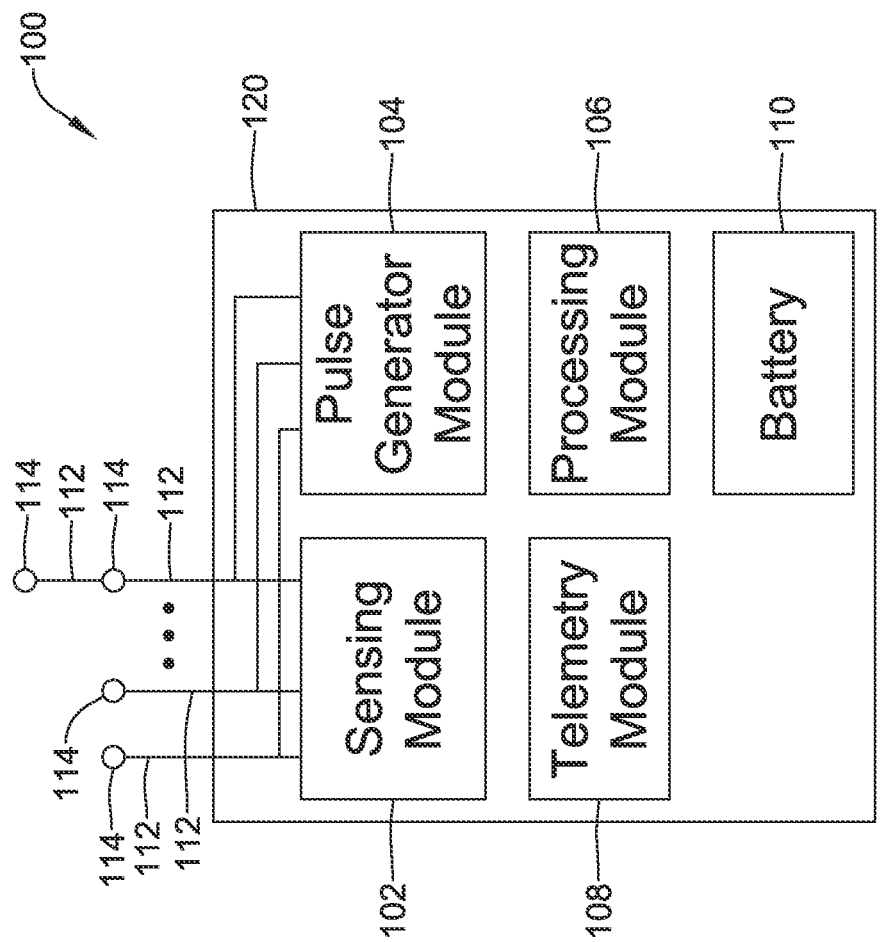
FIG. 1 illustrates a block diagram of an exemplary medical device that may be used in accordance with various examples of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart is almost completely desynchronized and the heart pumps very little to no blood.

Many medical device systems have been developed to assist patients who experience such abnormities. For example, systems have been developed to sense intrinsic cardiac electrical signals and, based on the sensed electrical signals, determine whether the patient is suffering from one or more arrhythmias. Such systems may also include the ability to deliver electrical stimulation to the heart of the patient in order to treat the detected arrhythmias. In one example, some medical device systems include the ability to identify when the heart is beating at too low of a rate, termed bradycardia. Such systems may deliver electrical stimulation therapy, or "pacing" pulses, that cause the heart to contract at a higher, safer rate. Some medical device systems are able to determine when a heart is beating at too fast of a rate, termed tachycardia. Such systems may further include one or more anti-tachycardia pacing (ATP) therapies. One such ATP therapy includes delivering electrical stimulation pulses to the heart at a rate faster than the intrinsically generated signals. Although this may temporarily cause the heart to beat faster, such a stimulation protocol may cause the heart to contract in response to the delivered pacing pulses as opposed to the intrinsically generated signals. The ATP therapy may then slow down the rate of the delivered pacing pulses, thereby reducing the heart rate to a lower, safer level.

Other medical device systems may be able to detect fibrillation states and asynchronous contractions. For example, based on the sensed signals, some systems may be able to determine when the heart is in a fibrillation state. Such systems may further be configured to treat such fibrillation states with electrical stimulation therapy. One such therapy includes deliver of a relatively large amount of electrical energy to the heart (a "defibrillation pulse") with the goal of overpowering any intrinsically generated signals. Such a therapy may "reset" the heart, from an electrical standpoint, which may allow for normal electrical processes to take over. Other medical systems may be able to sense that intrinsically generated signals are generated at differing times or that the heart conducts such signals at differing rates. These abnormalities may result in an unsynchronized, inefficient cardiac contraction. The system may further include the ability to administer one or more cardiac resynchronization therapies (CRTs). One such CRT may include delivering electrical stimulation to the heart at differing locations on and/or within the heart. Such methods may help the disparate parts of the heart to contract near simultaneously, or in a synchronized manner if the system delivers the electrical stimulation to the disparate locations at differing times.

The present disclosure relates generally to systems and methods for coordinating detection and/or treatment of abnormal heart activity using multiple implanted devices within a patient. In some instances, a medical device system may include a plurality of devices for detecting cardiac arrhythmias and delivering electrical stimulation therapy. For example, illustrative systems may include devices such as subcutaneous cardioverter-defibrillators (S-ICD), external cardioverter-defibrillators, implantable cardiac pacemakers (ICP), leadless cardiac pacemakers (LCPs), diagnostic only devices (devices that may sense cardiac electrical signals and/or determine arrhythmias but do not deliver electrical stimulation therapies) and/or neural stimulation devices.

FIG. 1 illustrates a block diagram of an exemplary medical device 100 (referred to hereinafter as, MD 100) that may be used in accordance with various examples of the present disclosure. In some cases, the MD 100 may be used for sensing intrinsic cardiac activity, determining occurrences of arrhythmias, and delivering electrical stimulation in response to determining an occurrence of an arrhythmia. In some instances, MD 100 can be implanted within a patient's body, at a particular location (e.g., in close proximity to the patient's heart), to sense and/or regulate the cardiac activity of the heart. In other examples, MD 100 may be located externally to a patient to sense and/or regulate the cardiac activity of the heart. In one example, cardiac contractions generally result from electrical signals that are intrinsically generated by a heart. These electrical signals conduct through the heart tissue, causing the muscle cells of the heart to contract. MD 100 may include features that allow MD 100 to sense such electrical signals and/or other physical parameters (e.g. mechanical contraction, heart sounds, blood pressure, blood-oxygen levels, etc.) of the heart. Such electrical signals and/or physical properties may be considered "cardiac activity." MD 100 may include the ability to determine occurrences of arrhythmias based on the sensed cardiac activity. In some examples, MD 100 may be able to deliver electrical stimulation to the heart in order to treat any detected arrhythmias. For example, MD 100 may be configured to deliver electrical stimulation, pacing pulses, defibrillation pulses, and/or the like in order to implement one or more therapies, such as bradycardia therapy, ATP therapy, CRT, defibrillation, or other electrical stimulation therapies.

FIG. 1 is an illustration of one example medical device 100. The illustrative MD 100 may include a sensing module 102, a pulse generator module 104, a processing module 106, a telemetry module 108, and a battery 110, all housed within a housing 120. MD 100 may further include leads 112, and electrodes 114 attached to housing 120 and in electrical communication with one or more of the modules 102, 104, 106, and 108 housed within housing 120.

Leads 112 may be connected to and extend away from housing 120 of MD 100. In some examples, leads 112 are implanted on or within the heart of the patient. Leads 112 may contain one or more electrodes 114 positioned at various locations on leads 112 and distances from housing 120. Some leads 112 may only include a single electrode 114 while other leads 112 may include multiple electrodes 114. Generally, electrodes 114 are positioned on leads 112 such that when leads 112 are implanted within the patient, one or more electrodes 114 are in contact with the patient's cardiac tissue. Accordingly, electrodes 114 may conduct intrinsically generated electrical signals to leads 112. Leads 112 may, in turn, conduct the received electrical signals to one or more modules 102, 104, 106, and 108 of MD 100. In a similar manner, MD 100 may generate electrical stimulation, and leads 112 may conduct the generated electrical stimulation to electrodes 114. Electrodes 114 may then conduct the electrical signals to the cardiac tissue of the patient. When discussing sensing intrinsic signals and delivering electrical stimulation, this disclosure may consider such conduction implicit in those processes.

Sensing module 102 may be configured to sense the cardiac electrical activity of the heart. For example, sensing module 102 may be connected to leads 112 and electrodes 114 through leads 112 and sensing module 102 may be configured to receive cardiac electrical signals conducted through electrodes 114 and leads 112. In some examples, leads 112 may include various sensors, such as accelerometers, blood pressure sensors, heart sound sensors, blood-oxygen sensors, and other sensors which measure physiological parameters of the heart and/or patient. In other examples, such sensors may be connected directly to sensing module 102 rather than to leads 112. In any case, sensing module 102 may be configured to receive such signals produced by any sensors connected to sensing module 102, either directly or through leads 112. Sensing modules 102 may additionally be connected to processing module 106 and may be configured to communicate such received signals to processing module 106.

Pulse generator module 104 may be connected to electrodes 114. In some examples, pulse generator module 104 may be configured to generate an electrical stimulation signals to provide electrical stimulation therapy to the heart. For example, pulse generator module 104 may generate such a signal by using energy stored in battery 110 within MD 100. Pulse generator module 104 may be configured to generate electrical stimulation signals in order to provide one or multiple of a number of different therapies. For example, pulse generator module 104 may be configured to generate electrical stimulation signals to provide bradycardia therapy, tachycardia therapy, cardiac resynchronization therapy, and fibrillation therapy. Bradycardia therapy may include generating and delivering pacing pulses at a rate faster than the intrinsically generated electrical signals in order to try to increase the heart rate. Tachycardia therapy may include ATP therapy as described herein. Cardiac resynchronization therapy may include CRT therapy also described herein. Fibrillation therapy may include delivering a fibrillation pulse to try to override the heart and stop the fibrillation state. In other examples, pulse generator 104 may be configured to generate electrical stimulation signals to provide electrical stimulation therapies different than those described herein to treat one or more detected arrhythmias.

Processing module 106 can be configured to control the operation of MD 100. For example, processing module 106 may be configured to receive electrical signals from sensing module 102. Based on the received signals, processing module 106 may be able to determine occurrences of arrhythmias. Based on any determined arrhythmias, processing module 106 may be configured to control pulse generator module 104 to generate electrical stimulation in accordance with one or more therapies to treat the determined one or more arrhythmias. Processing module 106 may further receive information from telemetry module 108. In some examples, processing module 106 may use such received information in determining whether an arrhythmia is occurring or to take particular action in response to the information. Processing module 106 may additionally control telemetry module 108 to send information to other devices.

In some examples, processing module 106 may include a pre-programmed chip, such as a very-large-scale integration (VLSI) chip or an application specific integrated circuit (ASIC). In such embodiments, the chip may be pre-programmed with control logic in order to control the operation of MD 100. By using a pre-programmed chip, processing module 106 may use less power than other programmable circuits while able to maintain basic functionality, thereby increasing the battery life of MD 100. In other examples, processing module 106 may include a programmable microprocessor. Such a programmable microprocessor may allow a user to adjust the control logic of MD 100, thereby allowing for greater flexibility of MD 100 than when using a pre-programmed chip. In some examples, processing module 106 may further include a memory circuit and processing module 106 may store information on and read information from the memory circuit. In other examples, MD 100 may include a separate memory circuit (not shown) that is in communication with processing module 106, such that processing module 106 may read and write information to and from the separate memory circuit.

Telemetry module 108 may be configured to communicate with devices such as sensors, other medical devices, or the like, that are located externally to MD 100. Such devices may be located either external or internal to the patient's body. Irrespective of the location, external devices (i.e. external to the MD 100 but not necessarily external to the patient's body) can communicate with MD 100 via telemetry module 108 to accomplish one or more desired functions. For example, MD 100 may communicate sensed electrical signals to an external medical device through telemetry module 108. The external medical device may use the communicated electrical signals in determining occurrences of arrhythmias. MD 100 may additionally receive sensed electrical signals from the external medical device through telemetry module 108, and MD 100 may use the received sensed electrical signals in determining occurrences of arrhythmias. Telemetry module 108 may be configured to use one or more methods for communicating with external devices. For example, telemetry module 108 may communicate via radiofrequency (RF) signals, inductive coupling, optical signals, acoustic signals, conducted communication signals, or any other signals suitable for communication. Communication techniques between MD 100 and external devices will be discussed in further detail with reference to FIG. 3 below.

Battery 110 may provide a power source to MD 100 for its operations. In one example, battery 110 may be a non-rechargeable lithium-based battery. In other examples, the non-rechargeable battery may be made from other suitable materials know in the art. Because, in examples where MD 100 is an implantable device, access to MD 100 may be limited, it is necessary to have sufficient capacity of the battery to deliver sufficient therapy over a period of treatment such as days, weeks, months, or years. In other examples, battery 110 may a rechargeable lithium-based battery in order to facilitate increasing the useable lifespan of MD 100.

In general, MD 100 may be similar to one of a number of existing medical devices. For example, MD 100 may be similar to various implantable medical devices. In such examples, housing 120 of MD 100 may be implanted in a transthoracic region of the patient. Housing 120 may generally include any of a number of known materials that are safe for implantation in a human body and may, when implanted, hermetically seal the various components of MD 100 from fluids and tissues of the patient's body.

In some examples, MD 100 may be an implantable cardiac pacemaker (ICP). In such an example, MD 100 may have one or more leads, for example leads 112, which are implanted on or within the patient's heart. The one or more leads 112 may include one or more electrodes 114 that are in contact with cardiac tissue and/or blood of the patient's heart. MD 100 may also be configured to sense intrinsically generated cardiac electrical signals and determine, for example, one or more cardiac arrhythmias based on analysis of the sensed signals. MD 100 may further be configured to deliver CRT, ATP therapy, bradycardia therapy, defibrillation therapy and/or other therapy types via leads 112 implanted within the heart.

In some instances, MD 100 may be a subcutaneous cardioverter-defibrillator (S-ICD). In such examples, one of leads 112 may include a subcutaneously implanted lead. In some cases, MD 100 may be configured to sense intrinsically generated cardiac electrical signals and determine one or more cardiac arrhythmias based on analysis of the sensed signals. MD 100 may further be configured to deliver one or more defibrillation pulses in response to determining an arrhythmia.

Figure 2:
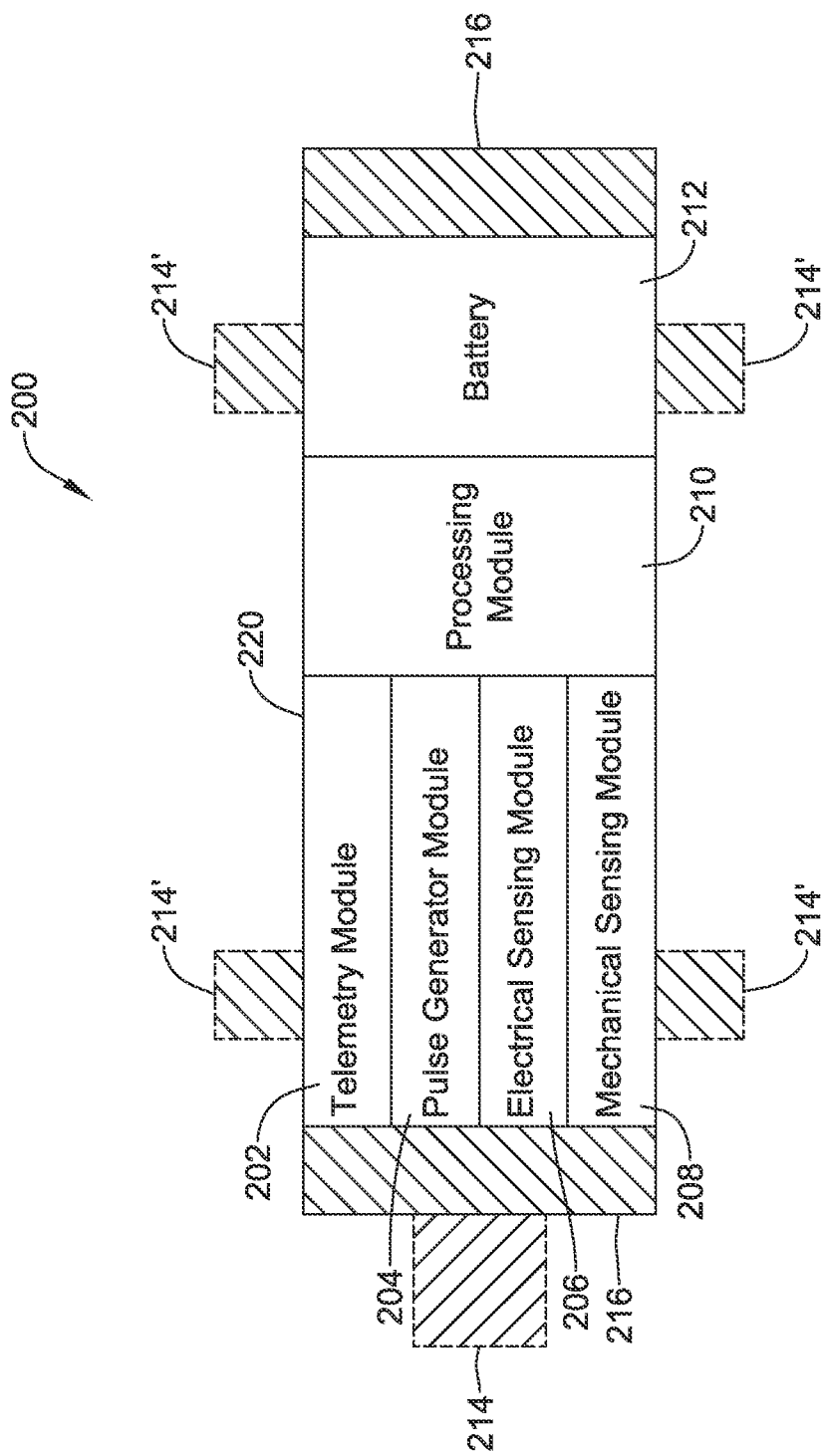
FIG. 2 illustrates an exemplary leadless cardiac pacemaker (LCP) having electrodes, according to one example of the present disclosure.

In still other examples, MD 100 may be a leadless cardiac pacemaker (LCP—described more specifically with respect to FIG. 2). In such examples, MD 100 may not include leads 112 that extend away from housing 120. Rather, MD 100 may include electrodes 114 coupled relative to the housing 120. In these examples, MD 100 may be implanted on or within the patient's heart at a desired location, and may be configured to deliver CRT, ATP therapy, bradycardia therapy, and/or other therapy types via electrodes 114.

In some instances, MD 100 may be a diagnostic-only device. In some cases, MD 100 may be configured to sense, or receive, cardiac electrical signals and/or physical parameters such as mechanical contraction, heart sounds, blood pressure, blood-oxygen levels, etc. MD 100 may further be configured to determine occurrences of arrhythmias based on the sensed or received cardiac electrical signals and/or physical parameters. In one example, MD 100 may do away with pulse generation module 104, as MD 100 may not be configured to deliver electrical stimulation in response to determining an occurrence of an arrhythmia. Rather, in order to respond to detected cardiac arrhythmias, MD 100 may be part of a system of medical devices. In such a system, MD 100 may communicate information to other devices within the system and one or more of the other devices may take action, for example delivering electrical stimulation therapy, in response to the receive information from MD 100. The term pulse generator may be used to describe any such device that is capable of delivering electrical stimulation therapy to the heart, such as an ICD, ICP, LCP, or the like.

In some example, MD 100 may not be an implantable medical device. Rather, MD 100 may be a device external to the patient's body, and may include skin-electrodes that are placed on a patient's body. In such examples, MD 100 may be able to sense surface cardiac electrical signals (e.g. electrical signals that are generated by the heart or device implanted within a patient's body and conducted through the body to the skin). In such examples, MD 100 may still be configured to deliver various types of electrical stimulation therapy. In other examples, however, MD 100 may be a diagnostic-only device.

FIG. 2 is an illustration of an exemplary leadless cardiac pacemaker (LCP) 200. In the example shown, LCP 200 may include all of the modules and components of MD 100, except that LCP 200 may not include leads 112. As can be seen in FIG. 2, LCP 200 may be a compact device with all components housed within LCP 200 or directly on housing 220. As illustrated in FIG. 2, LCP 200 may include telemetry module 202, pulse generator module 204, processing module 210, and battery 212. Such components may have a similar function to the similarly named modules and components as discussed in conjunction with MD100 of FIG. 1.

In some examples, LCP 200 may include electrical sensing module 206 and mechanical sensing module 208. Electrical sensing module 206 may be similar to sensing module 102 of MD 100. For example, electrical sensing module 206 may be configured to receive electrical signals generated intrinsically by the heart. Electrical sensing module 206 may be in electrical connection with electrodes 214, which may conduct the intrinsically generated electrical signals to electrical sensing module 206. Mechanical sensing module 208 may be configured to receive one or more signals representative of one or more physiological parameters of the heart. For example, mechanical sensing module 208 may include, or be in electrical communication with one or more sensors, such as accelerometers, blood pressure sensors, heart sound sensors, blood-oxygen sensors, and other sensors which measure physiological parameters of the patient. Although described with respect to FIG. 2 as separate sensing modules, in some examples, electrical sensing module 206 and mechanical sensing module 208 may be combined into a single module.

In at least one example, each of modules 202, 204, 206, 208, and 210 illustrated in FIG. 2 may be implemented on a single integrated circuit chip. In other examples, the illustrated components may be implemented in multiple integrated circuit chips that are in electrical communication with one another. All of modules 202, 204, 206, 208, and 210 and battery 212 may be encompassed within housing 220. Housing 220 may generally include any material that is known as safe for implantation within a human body and may hermetically seal modules 202, 204, 206, 208, and 210 and battery 212 from fluids and tissues when LCP 200 is implanted within a patient.

As depicted in FIG. 2, LCP 200 may include electrodes 214, which can be secured relative to housing 220 but exposed to the tissue and/or blood surrounding the LCP 200. As such, electrodes 214 may be generally disposed on either end of LCP 200 and may be in electrical communication with one or more of modules 202, 204, 206, 208, and 210. In some examples, electrodes 214 may be connected to housing 220 only through short connecting wires such that electrodes 214 are not directly secured relative to housing 220. In some examples, LCP 200 may additionally include one or more electrodes 214'. Electrodes 214' may be positioned on the sides of LCP 200 and increase the number of electrodes by which LCP 200 may sense cardiac electrical activity and/or deliver electrical stimulation. Electrodes 214 and/or 214' can be made up of one or more biocompatible conductive materials such as various metals or alloys that are known to be safe for implantation within a human body. In some instances, electrodes 214 and/or 214' connected to LCP 200 may have an insulative portion that electrically isolates the electrodes 214 from, adjacent electrodes, the housing 220, and/or other materials.

To implant LCP 200 inside patient's body, an operator (e.g., a physician, clinician, etc.), may need to fix LCP 200 to the cardiac tissue of the patient's heart. To facilitate fixation, LCP 200 may include one or more anchors 216. Anchor 216 may be any one of a number of fixation or anchoring mechanisms. For example, anchor 216 may include one or more pins, staples, threads, screws, helix, tines, and/or the like. In some examples, although not shown, anchor 216 may include threads on its external surface that may run along at least a partial length of anchor 216. The threads may provide friction between the cardiac tissue and the anchor to help fix anchor 216 within the cardiac tissue. In other examples, anchor 216 may include other structures such as barbs, spikes, or the like to facilitate engagement with the surrounding cardiac tissue.

The design and dimensions of MD 100 and LCP 200, as shown in FIGS. 1 and 2, respectively, can be selected based on various factors. For example, if the medical device is for implant on the endocardial tissue, such as is sometimes the case of an LCP, the medical device can be introduced through a femoral vein into the heart. In such instances, the dimensions of the medical device may be such as to be navigated smoothly through the tortuous path of the vein without causing any damage to surrounding tissue of the vein. According to one example, the average diameter of the femoral vein may be between about 4 mm to about 8 mm in width. For navigation to the heart through the femoral vein, the medical device can have a diameter of at less than 8 mm. In some examples, the medical device can have a cylindrical shape having a circular cross-section. However, it should be noted that the medical device can be made of any other suitable shape such as rectangular, oval, etc. A flat, rectangular-shaped medical device with a low profile may be desired when the medical device is designed to be implanted subcutaneously.

FIGS. 1 and 2 above described various examples of MD 100. In some examples, a medical device system may include more than one medical device. For example, multiple medical devices 100/200 may be used cooperatively to detect and treat cardiac arrhythmias and/or other cardiac abnormalities. Some example systems will be described below in connection with FIGS. 3-10. In such multiple device systems, it may be desirable to have a medical device communicate with another medical device, or at least receive various communication signals from another medical device.

Figure 3:
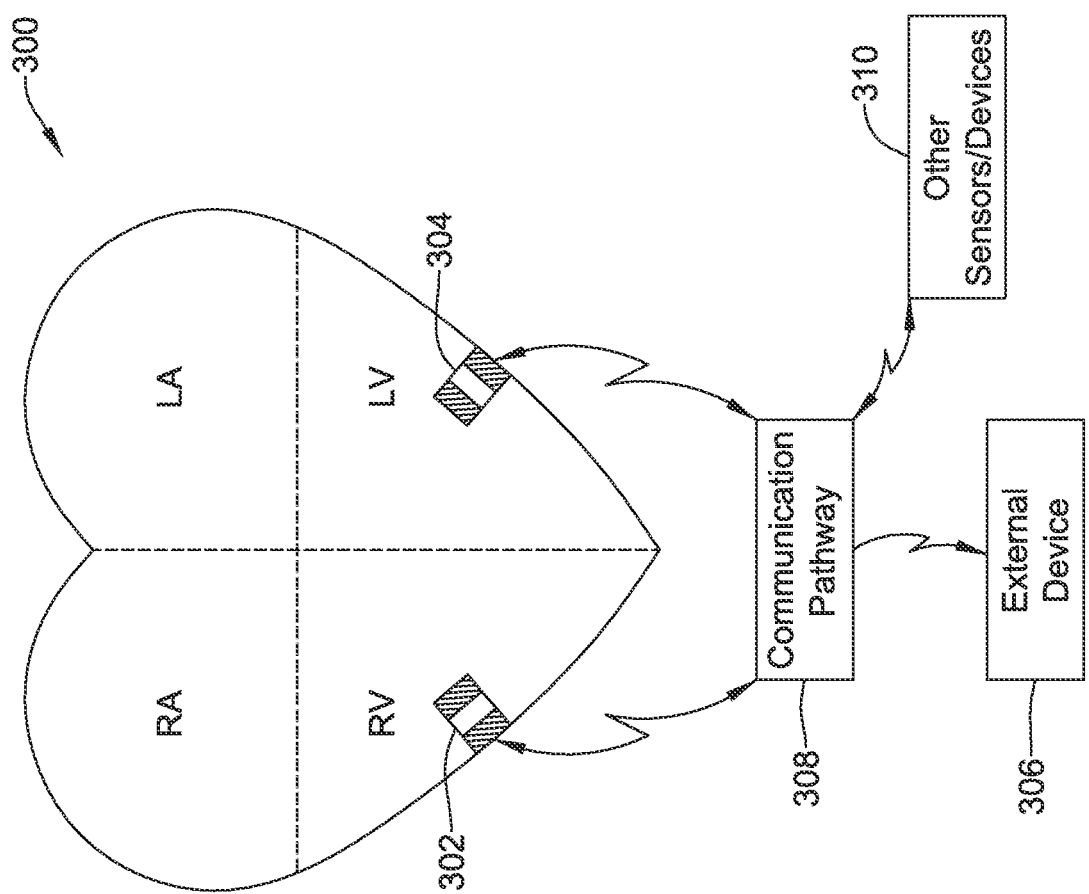
FIG. 3 is a schematic diagram of an exemplary medical system that includes multiple leadless cardiac pacemakers (LCPs) and/or other devices in communication with one another of the present disclosure.

FIG. 3 illustrates an example of a medical device system and a communication pathway via which multiple medical devices may communicate. In the example shown, medical device system 300 may include LCPs 302 and 304, external medical device 306, and other sensors/devices 310. External device 306 may be any of the devices described previously with respect to MD 100. Other sensors/devices 310 may also be any of the devices described previously with respect to MD 100. In other examples, other sensors/devices 310 may include a sensor, such as an accelerometer or blood pressure sensor, or the like. In still other examples, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, external device 306 may receive such signals and, based on the received signals, determine an occurrence of an arrhythmia. In some cases, external device 306 may communicate such determinations to one or more other devices 302/304, 306, and 310 of system 300. Additionally, one or more other devices 302/304, 306, and 310 of system 300 may take action based on the communicated determination of an arrhythmia, such as by delivering a suitable electrical stimulation. This description is just one of many reasons for communication between the various devices of system 300.

Communication pathway 308 may represent one or more of various communication methods. For example, the devices of system 300 may communicate with each other via RF signals, inductive coupling, optical signals, acoustic signals, or any other signals suitable for communication and communication pathway 308 may represent such signals.

In at least one example, communicated pathway 308 may represent conducted communication signals. Accordingly, devices of system 300 may have components that allow for conducted communication. In examples where communication pathway 308 includes conducted communication signals, devices of system 300 may communicate with each other by sensing electrical communication pulses delivered into the patient's body by another device. The patient's body may conduct these electrical communication pulses to the other devices of system 300. In such examples, the delivered electrical communication pulses may differ from the electrical stimulation pulses of any of the above described electrical stimulation therapies. For example, the devices of system 300 may deliver such electrical communication pulses at a voltage level that is sub-threshold. That is, the voltage amplitude of the delivered electrical communication pulses may be low enough as to not capture the heart (e.g. not cause a contraction). Although, in some circumstances, one or more delivered electrical communication pulses may capture the heart, and in other circumstances, delivered electrical stimulation pulses may not capture the heart. In some cases, the delivered electrical communication pulses may be modulated (e.g. pulse width modulated), or the timing of the delivery of the communication pulses may be modulates, to encode the communicated information. These are just some examples.

As mentioned above, some example systems may employ multiple devices for determining occurrences of arrhythmias, and/or for delivering electrical stimulation therapy in response to determining one or more arrhythmias. In some embodiments employing multiple devices, one or more of the multiple devices may, for example, detect an occurrence of arrhythmia while one or more different devices may deliver an anti-tachycardia pacing therapy. In some embodiments, a first medical device may communicate a need for assistance to a second medical device, and the second medical device may work with the first medical device to deliver a more effective pacing therapy. In some embodiments, a second medical device may instead be instructed by the first medical device to temporarily cease operation while the first medical device delivers an anti-tachycardia pacing or other therapy.

For example, if a patient has an atrial LCP and a ventricular LCP, it may be advantageous for the atrial LCP to be inhibited while the ventricular LCP delivers anti-tachycardia pacing therapy to the patient's heart. In some embodiments, such as in a CRT therapy situation, some patients respond better to pacing therapy delivered to both the left ventricle and the right ventricle. It is advantageous in these situations to coordinate ant-tachycardia pacing therapy between the LCP disposed in or near the left ventricle and the LCP disposed in or near the right ventricle. If present, an atrial LCP is inhibited during the anti-tachycardia pacing therapy. In contrast, some patients may respond better to anti-tachycardia pacing therapy delivered only to a single ventricle. In such instances, either the left ventricle LCP or the right ventricle LCP may deliver anti-tachycardia pacing therapy while the other ventricular LCP may be inhibited. Any atrial LCP, if present, may be inhibited. In some embodiments, if an S-ICD is present and a need for defibrillation is determined, the LCPs present in or near the patient's heart may be instructed to cease operation, and possibly isolate their internal circuits from their input/output electrodes (rendering the electrodes inactive) for their own protection, before the S-ICD delivers a defibrillation shock.

FIG. 3, for example, shows LCP 302 disposed in the right ventricle and LCP 304 disposed in the left ventricle. If a need for anti-tachycardia pacing therapy is determined, in some embodiments, one of the LCPs 302, 304 may instruct the other LCP to assist in providing biventricular anti-tachycardia pacing therapy. In some embodiments, LCP 302 may provide right ventricular anti-tachycardia pacing therapy while LCP 304 remains dormant. In some embodiments, LCP 304 may provide left ventricular anti-tachycardia pacing therapy while LCP 302 remains dormant. In some embodiments, both LCP 302 and LCP 304 may be instructed to remain dormant while another device provides pacing therapy.

FIGS. 3-10 describe various example systems that may use multiple devices in order to determine occurrences of arrhythmias and/or deliver electrical stimulation therapy. However, FIGS. 3-10 should not be viewed as limiting examples. For example, FIGS. 3-10 describe how various multiple device systems may coordinate to detect various arrhythmias. However, any combinations of devices such as that described with respect to MD 100 and LCP 200 may be used in concert with the below described techniques for detecting arrhythmias. Additionally, although the below description focuses on how devices of various systems may operate to detect arrhythmias, such devices may additionally operate to deliver electrical stimulation therapy in accordance with one or more techniques, such as described in the co-pending U.S. patent application Ser. No. 14/592,723 titled "SYSTEMS AND METHODS FOR TREATING CARDIAC ARRHYTHMIAS, filed Jan. 8, 2015, published as US 2015/0196756, which application is hereby incorporated by reference in its entirety.

Figure 4:
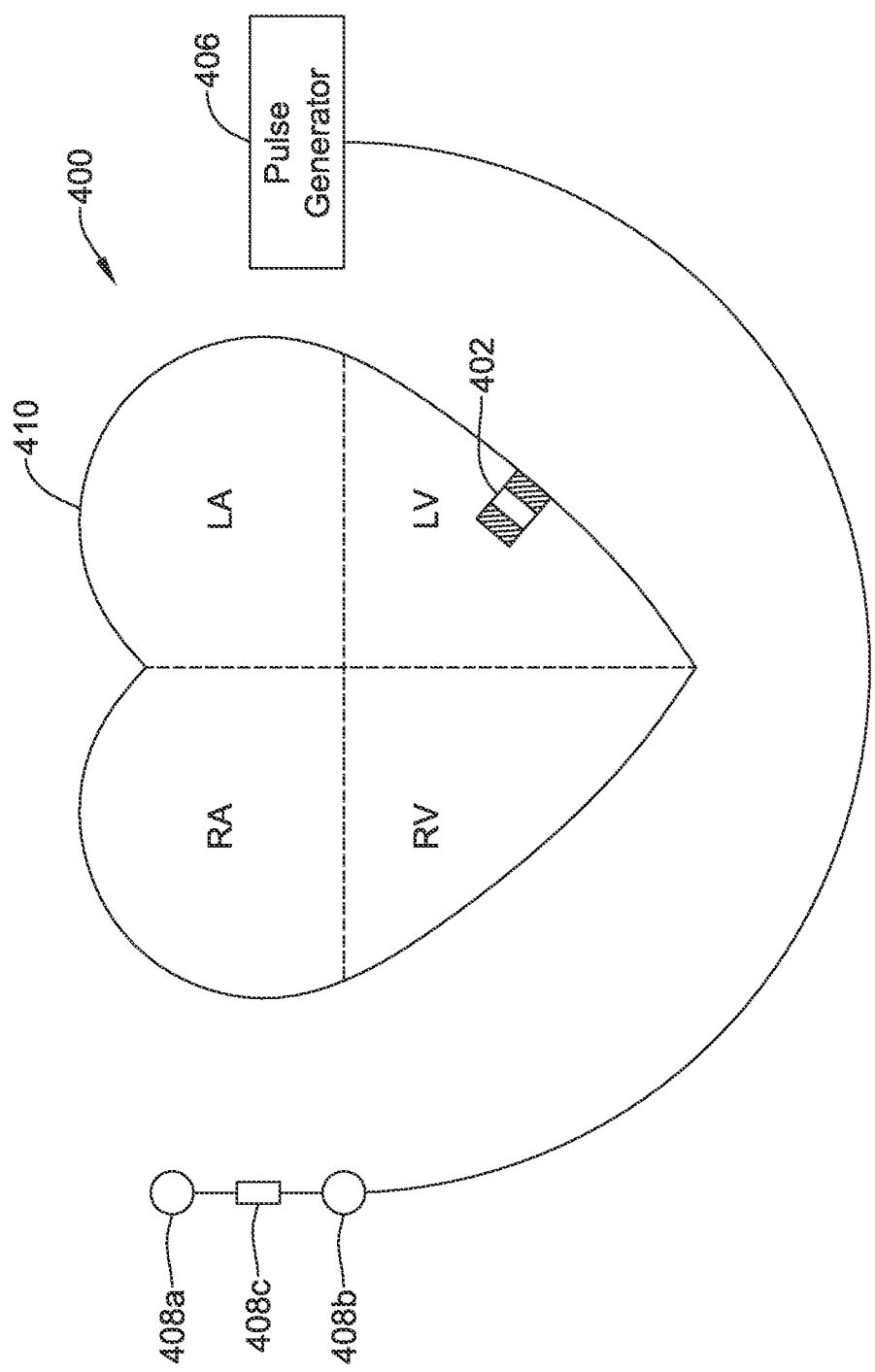
FIG. 4 is a schematic diagram of a system including an LCP and another medical device, in accordance with yet another example of the present disclosure.

FIG. 4 illustrates an example medical device system 400 that includes an LCP 402 and a pulse generator 406. In some examples, pulse generator 406 may be either an external cardioverter-defibrillator or an ICD. For example, pulse generator 406 may be such devices as described previously with respect to MD 100. In some examples, pulse generator 406 may be an S-ICD. In examples where pulse generator 406 is an external cardioverter-defibrillator, electrodes 408a, 408b, and 408c may be skin electrodes that reside on the patient's body. In examples where pulse generator 406 is an S-ICD, electrodes 408a, 408b, and 408c may be attached to a subcutaneous lead that is implanted within the patient's body proximate, but not on or within the heart 410.

As shown, LCP 402 may be implanted within heart 410. Although LCP 402 is depicted as being implanted within the left ventricle (LV) of heart 410, in other examples, LCP 402 may be implanted within a different chamber of the heart 410. For example, LCP 402 may be implanted within the left atrium (LA) of heart 410 or the right atrium (RA) of heart 410. In other examples, LCP 402 may be implanted within the right ventricle (RV) of heart 410.

In any event, LCP 402 and pulse generator 406 may operate together to determine occurrences of cardiac arrhythmias of heart 410. In some instances, devices 402 and 406 may operate independently to sense cardiac activity of heart 410. As described above, cardiac activity may include sensed cardiac electrical signals and/or sensed physiological parameters. In such examples, each of LCP 402 and pulse generator 406 may operate to determine occurrences of arrhythmias independently of one another based on the independently sensed cardiac activity. When a first of LCP 402 or pulse generator 406 makes a first determination of an arrhythmia, that first device may communicate the first determination to the second device. If the second device of system 400 also makes a determination of an arrhythmia, e.g. a second determination of an arrhythmia, based on its own sensed cardiac activity, the arrhythmia may be confirmed and the system 400 may begin to deliver appropriate electrical stimulation therapy to heart 410. In this manner, both devices 402 and 406 of system 400 may be used to determine an occurrence of an arrhythmia. In some examples, when only one of devices 402 or 406 determines an occurrence of an arrhythmia, and the other does not, system 400 may still begin to deliver appropriate electrical stimulation therapy to heart 410.

In other examples, only one of devices 402 and 406 actively senses cardiac activity and determines occurrences of arrhythmias. For example, when the actively sensing device (e.g. LCP 402) determines an occurrence of an arrhythmia, the actively sensing device may communicate the determination to the other device (e.g. Pulse Generator 406) of system 400. System 400 may then begin to deliver appropriate electrical stimulation therapy to heart 410. In another example, the device which actively senses cardiac activity may communicate the sensed cardiac activity to the other device. Then, based on the received cardiac activity, the other device may determine an occurrence of an arrhythmia. System 400 may then begin to deliver appropriate electrical stimulation therapy to heart 410. In some of these examples, the other device may additionally communicate the determination of an arrhythmia to the actively sensing device.

In still other examples, only a first of devices 402 or 406 continuously senses cardiac actively. The first device (e.g. Pulse Generator 406) may continually determine, based on the sensed cardiac activity, occurrences of arrhythmias. In such examples, when the first device determines an occurrence of an arrhythmia, the first device may communicate the determination to the second device (e.g. LCP 402). Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia, system 400 may begin to deliver appropriate electrical stimulation therapy to heart 410.

In some examples, determining an occurrence of an arrhythmia may include determining a beginning of an arrhythmia, and system 400 may be configured to determine when to begin to deliver electrical stimulation therapy. In some examples, determining an occurrence of an arrhythmia may include determining an end of an arrhythmia. In such examples, system 400 may be configured to also determine when to cease to deliver electrical stimulation therapy.

In examples where system 400 operates to deliver appropriate electrical stimulation therapy to heart 410, if the determined arrhythmia is a fibrillation, pulse generator 406 may operate to deliver a defibrillation pulse to heart 410. In examples where the determined arrhythmia is a tachycardia, LCP 402 may deliver ATP therapy to heart 410. In examples where the determined arrhythmia is a bradycardia, LCP 402 may deliver bradycardia therapy to heart 410. In examples where the determined arrhythmia is un-synchronized contractions, LCP 402 may deliver CRT to heart 410.

Figure 5:
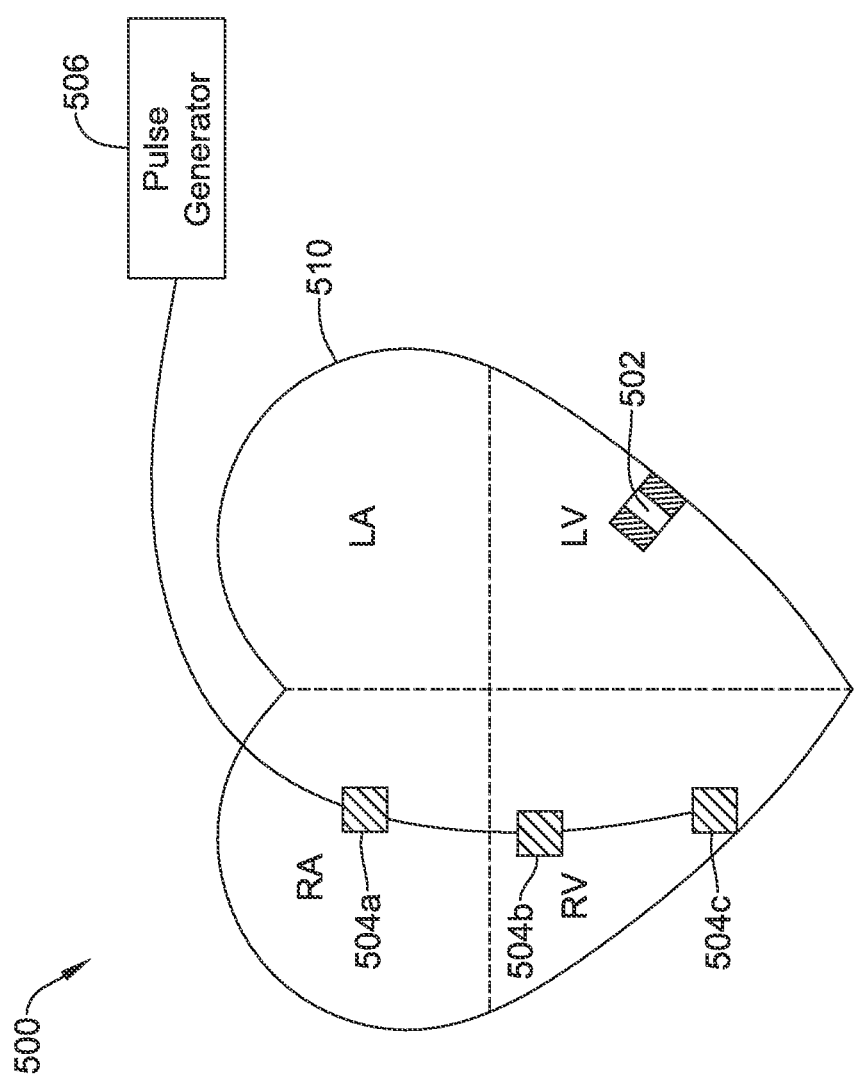
FIG. 5 is a schematic diagram of the a system including an LCP and another medical device, in accordance with another example of the present disclosure.

FIG. 5 illustrates an example medical device system 500 that includes an LCP 502 and a pulse generator 506. In this example, pulse generator 506 may be an implantable cardiac pacemaker (ICP). For example, pulse generator 506 may be an ICP such as that described previously with respect to MD 100. In examples where pulse generator 506 is an ICP, electrodes 504a, 504b, and 504c may be implanted on or within the right ventricle and/or right atrium of heart 510 via one or more leads.

LCP 502 may be implanted within heart 510. Although LCP 502 is depicted implanted within the left ventricle (LV) of the heart 510, in some instances, LCP 502 may be implanted within a different chamber of the heart 510. For example, LCP 502 may be implanted within the left atrium (LA) of heart 510 or the right atrium (RA) of heart 510. In other examples, LCP 502 may be implanted within the right ventricle (RV) of heart 510.

In any event, LCP 502 and pulse generator 506 may operate together to determine occurrences of cardiac arrhythmias of heart 510. In some instances, devices 502 and 506 may operate independently to sense cardiac activity of heart 510. As described above, cardiac activity may include sensed cardiac electrical signals and/or sensed physiological parameters. In some cases, each of LCP 502 and pulse generator 506 may operate to determine occurrences of arrhythmias independently based on the independently sensed cardiac activity. When a first of LCP 502 or pulse generator 506 makes a first determination of an arrhythmia, that first device may communicate the first determination to the second device. If the second device of system 500 also makes a determination of an arrhythmia, e.g. a second determination of an arrhythmia, based on its own sensed cardiac activity, system 500 may confirm the arrhythmia and may begin to deliver appropriate electrical stimulation therapy to heart 510. In this manner, both devices 502 and 506 of system 500 may be used to determine an occurrence of an arrhythmia. In some instances, when only a single one of devices 502 or 506 determines an occurrence of an arrhythmia, system 500 may also begin to deliver appropriate electrical stimulation therapy to heart 510.

In some examples, only one of devices 502 and 506 may actively sense cardiac activity and determine occurrences of arrhythmias. For example, when the actively sensing device (e.g. pulse generator 506) determines an occurrence of an arrhythmia, the actively sensing device may communicate the determination to the other device (e.g. LCP 502) of system 500. System 500 may then begin to deliver appropriate electrical stimulation therapy to heart 510. In some examples, the device which actively senses cardiac activity may communicate the sensed cardiac activity to the other device. Then, based on the received cardiac activity, the other device may sense for and determine an occurrence of an arrhythmia. System 500 may then begin to deliver appropriate electrical stimulation therapy to heart 510. In some instances, the other device may additionally communicate the determination of an arrhythmia to the actively sensing device.

In still other examples, only a first of devices 502 or 506 may continuously senses cardiac actively. The first device may additionally continually determine, based on the sensed cardiac activity, occurrences of arrhythmias. In some examples, when the first device determines an occurrence of an arrhythmia, the first device may communicate the determination to the second device. Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia, system 500 may begin to deliver appropriate electrical stimulation therapy to heart 510.

In some examples, determining an occurrence of an arrhythmia may include determining a beginning of an arrhythmia, and system 500 may be configured to determine when to begin to deliver electrical stimulation therapy. In some examples, determining an occurrence of an arrhythmia may include determining an end of an arrhythmia. In such examples, system 500 may be configured to determine when to cease to deliver electrical stimulation therapy. In examples where system 500 does not begin to deliver appropriate electrical stimulation therapy to heart 510 until multiple devices determine an occurrence of a cardiac arrhythmia, each of the determinations that do not trigger delivery of electrical stimulation therapy may be termed provisional determinations.

In examples where system 500 operates to deliver appropriate electrical stimulation therapy to heart 510, if the determined arrhythmia is a tachycardia, either pulse generator 506, LCP 502, or both may deliver ATP therapy to heart 510. In examples where the determined arrhythmia is a bradycardia, either pulse generator 506, LCP 502, or both may deliver bradycardia therapy to heart 510. In examples where the determined arrhythmia is un-synchronized contractions, either pulse generator 506, LCP 502, or both may deliver CRT to heart 510.

Figure 6:
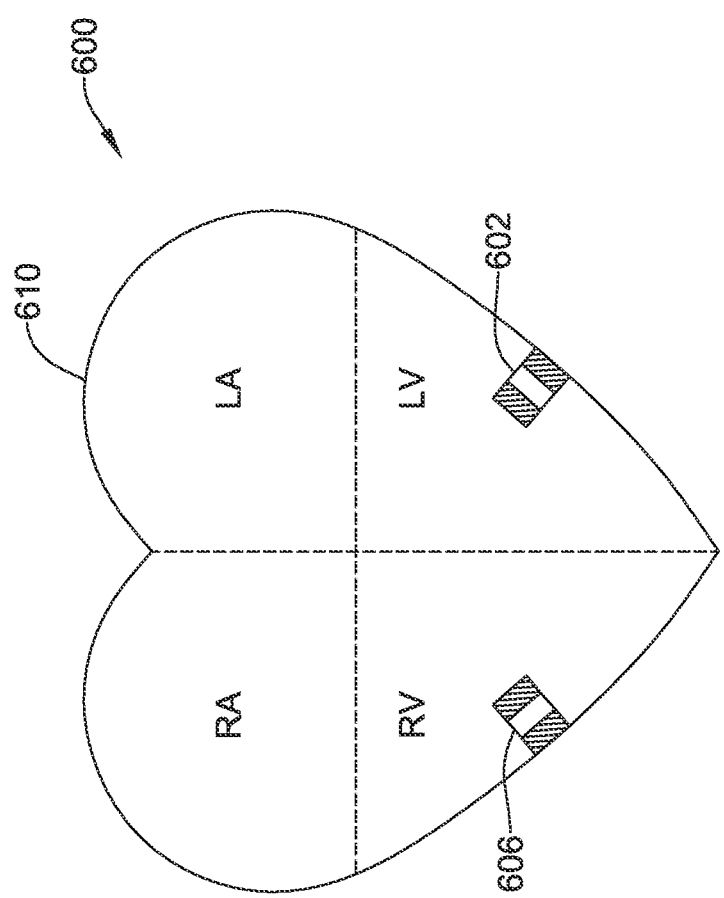
FIG. 6 is a schematic diagram illustrating a multiple leadless cardiac pacemaker (LCP) system in accordance with another example of the present disclosure.

FIG. 6 illustrates an example medical device system 600 that includes LCP 602 and LCP 606. LCP 602 and LCP 606 are shown implanted within heart 610. Although LCPs 602 and 606 are depicted as implanted within the left ventricle (LV) of heart 610 and the right ventricle of heart 610, respectively, in other examples, LCPs 602 and 606 may be implanted within different chambers of heart 610. For example, system 600 may include LCPs 602 and 606 implanted within both atria of heart 610. In other examples, system 600 may include LCPs 602 and 606 implanted within one atrium and one ventricle of heart 610. In more examples, system 600 may include LCPs 602 and 606 implanted within any combination of ventricles and atria. In yet other examples, system 600 may include LCPs 602 and 606 implanted within the same chamber of heart 610.

In any event, and in some examples, LCP 602 and LCP 606 may operate together to determine occurrences of cardiac arrhythmias of heart 610. For example, devices 602 and 606 may operate independently to sense cardiac activity of heart 610. As described above, cardiac activity may include sensed cardiac electrical signals and/or sensed physiological parameters. In such examples, each of LCP 602 and LCP 606 may operate to determine occurrences of arrhythmias independently based on the independently sensed cardiac activity. When a first of LCP 602 or LCP 606 makes a first determination of an arrhythmia, that first device may communicate the first determination to the second device. If the second device of system 600 also makes a determination of an arrhythmia, e.g. a second determination of an arrhythmia, based on its own sensed cardiac activity, system 600 may confirm the arrhythmia and may begin to deliver appropriate electrical stimulation therapy to heart 610. In this manner, both devices 602 and 606 of system 600 may be used to determine an occurrence of an arrhythmia. In some examples, when only a single one of devices 602 or 606 determines an occurrence of an arrhythmia, system 600 may begin to deliver appropriate electrical stimulation therapy to heart 610.

In other examples, only one of devices 602 and 606 may actively sense cardiac activity and determine occurrences of arrhythmias. In some of these examples, when the actively sensing device (e.g. LCP 606) determines an occurrence of an arrhythmia, the actively sensing device may communicate the determination to the other device (e.g. LCP 602) of system 600. System 600 may then begin to deliver appropriate electrical stimulation therapy to heart 610. In some cases, the device which actively senses cardiac activity may communicate the sensed cardiac activity to the other device. Then, based on the received cardiac activity, the other device may determine an occurrence of an arrhythmia. System 600 may then begin to deliver appropriate electrical stimulation therapy to heart 610. In some of these examples, the other device may additionally communicate the determination of an arrhythmia to the actively sensing device and/or to another device.

In some examples, only a first of devices 602 or 606 may continuously sense cardiac actively. The first device may continually determine, based on the sensed cardiac activity, occurrences of arrhythmias. In such examples, when the first device determines an occurrence of an arrhythmia, the first device may communicate the determination to the second device. Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia does system 600 begin to deliver appropriate electrical stimulation therapy to heart 610.

In some examples, determining an occurrence of an arrhythmia may include determining a beginning of an arrhythmia, and system 600 may be configured to determine when to begin to deliver electrical stimulation therapy. In some examples, determining an occurrence of an arrhythmia may include determining an end of an arrhythmia. In such examples, system 600 may be configured to also determine when to cease to deliver electrical stimulation therapy. In examples where system 600 does not begin to deliver appropriate electrical stimulation therapy to heart 610 until multiple devices determine an occurrence of a cardiac arrhythmia, each of the determinations that do not trigger delivery of electrical stimulation therapy may be termed provisional determinations.

In examples where system 600 operates to deliver appropriate electrical stimulation therapy to heart 610, if the determined arrhythmia is a tachycardia, either LCP 602, LCP 606, or both may deliver ATP therapy to heart 610. In examples where the determined arrhythmia is a bradycardia, either LCP 602, LCP 606, or both may deliver bradycardia therapy to heart 610. In examples where the determined arrhythmia is un-synchronized contractions, either LCP 602, LCP 606, or both may deliver CRT to heart 610.

In some embodiments, if a need for anti-tachycardia pacing therapy is determined, one of the LCPS 602, 606 may instruct the other LCP to assist in providing biventricular anti-tachycardia pacing therapy. In some embodiments, LCP 606 may provide right ventricular anti-tachycardia pacing therapy while LCP 602 remains dormant. In some embodiments, LCP 602 may provide left ventricular anti-tachycardia pacing therapy while LCP 606 remains dormant. In some embodiments, both LCP 602 and LCP 606 may be instructed to remain dormant while another device provides pacing therapy. These are just examples.

Although not necessarily described in FIGS. 4-6, one of the two devices of systems 400, 500, or 600 could be a diagnostic-only device. In such examples, after one or more of the devices determined an occurrence of an arrhythmia, the diagnostic-only device may not deliver any electrical stimulation therapy. Rather, electrical stimulation therapy may be delivered by another device in the system that is capable of delivering appropriate electrical stimulation therapy, if desired.

Figure 7:
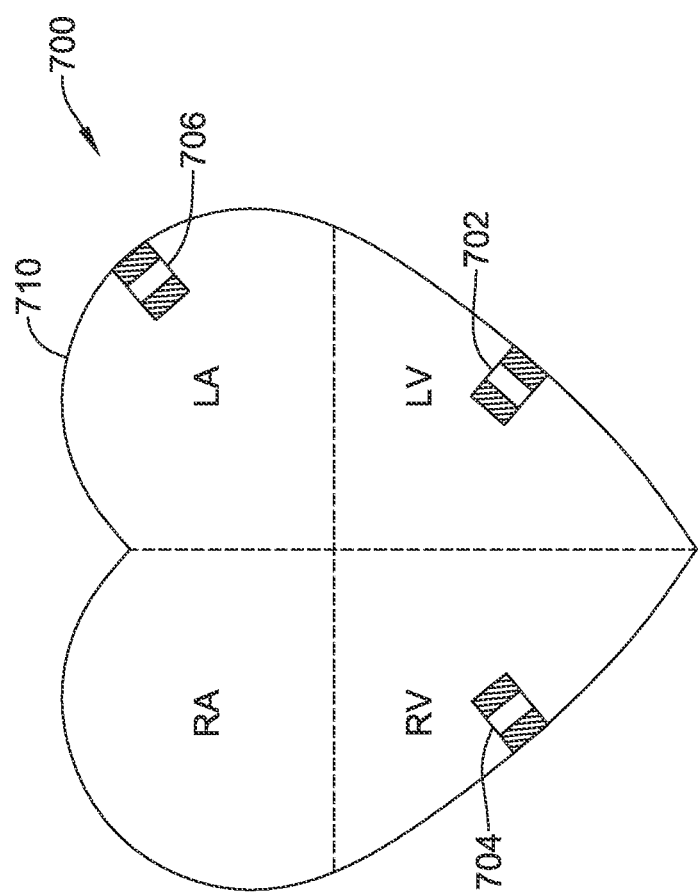
FIG. 7 is a schematic diagram illustrating a multiple leadless cardiac pacemaker (LCP) system, in accordance with yet another example of the present disclosure.

FIG. 7 illustrates an example medical device system 700 with three separate LCPs including LCP 702, LCP 704, and LCP 706. Although system 700 is depicted with LCPs 702, 704, and 706 implanted within the LV, RV, and LA, respectively, other examples may include LCPs 702, 704, and 706 implanted within different chambers of the heart 710. For example, system 700 may include LCPs implanted within both atria and one ventricle of the heart 710. In other examples, system 700 may include LCPs implanted within both ventricles and one atria of heart 710. More generally, it is contemplated that system 700 may include LCPs implanted within any combination of ventricles and atria. In some instances, system 700 may include two or more of LCPs 702, 704, and 706 implanted within the same chamber of the heart 710.

In practice, such a system 700 may operate in accordance with any of the techniques described above with respect to FIGS. 4-6. In some instances, however, system may operate differently, at least to some degree. For example, before system 700 begins to deliver appropriate electrical stimulation therapy to the heart 710, only a majority of LCPs 702, 704, and 706 may need to determine an occurrence of an arrhythmia. For example, in some instances, all of LCPs 702, 704, and 706 may be sensing cardiac activity and determining occurrences of arrhythmias independently. In some cases, only after a majority of LCPs 702, 704, and 706 determined an occurrence of an arrhythmia, may system 700 deliver appropriate electrical stimulation therapy to the heart 710. In some instances, one of the LCP's is designated as the master LCP, and the other slave LCP's may communicate whether they determine an occurrence of an arrhythmia to the master LCP. The master LCP may then determine if a majority of the LCP's 702, 704, and 706 have determined an occurrence of an arrhythmia, and if so, may instruct the delivery of appropriate electrical stimulation therapy to the heart 710. In some instances, the master LCP may instruct particular ones of the LCP's 702, 704, and 706 to deliver electrical stimulation therapy to the heart 710, depending on the type and/or location of the detected arrhythmia.

Alternatively, and in some instances, only a single LCP may need to determine an occurrence of an arrhythmia before system 700 may begin to deliver appropriate electrical stimulation therapy to heart 710. In yet other examples, all three of the LCP's 702, 704, and 706 may need to determine an occurrence of an arrhythmia before system 700 delivers appropriate electrical stimulation therapy to the heart 710.

In some cases, only one LCP 702, 704, and 706 may actively sense cardiac activity and determine an occurrence of an arrhythmia. After determining an occurrence of an arrhythmia, the actively sensing device may communicate the determination to one or both of the other devices. In some cases, one or both of the other devices may then begin sensing for and determining occurrences of arrhythmias. In some instances, when a first one of the other devices determines an occurrence of an arrhythmia, system 700 may begin to deliver appropriate electrical stimulation therapy to heart 710. In other instances, when both of the other devices determine an occurrence of an arrhythmia, system 700 may begin to deliver appropriate electrical stimulation therapy to heart 710.

In some instances, LCPs 702, 704, and 706 may be set up in a daisy-chain configuration. For example, an actively sensing device may send a determination of an arrhythmia to only one of the other two devices (alternatively, only one of the two receiving devices may act upon the received determination from the actively sensing device). The receiving device may then begin actively sensing for and determining occurrences of arrhythmias. Upon determining an occurrence of an arrhythmia, the receiving device may communicate the determination to the last device. The last device may then begin sensing for and determining occurrences of arrhythmias. In some instances, only when the last device determines an occurrence of an arrhythmia does the system 700 begin to deliver appropriate electrical stimulation therapy to heart 710.

Also in accord with the description of systems 400, 500, and 700, in some examples, determining an occurrence of an arrhythmia may include determining a beginning of an arrhythmia, and system 700 may be configured to determine when to begin to deliver electrical stimulation therapy. In some examples, determining an occurrence of an arrhythmia may include determining an end of an arrhythmia. In such examples, system 700 may be configured to determine when to cease delivery of electrical stimulation therapy. In examples where system 700 does not begin to deliver appropriate electrical stimulation therapy to heart 710 until multiple LCP devices determine an occurrence of an arrhythmia, each of the determinations that do not trigger delivery of electrical stimulation therapy may be termed provisional determinations.

In examples where system 700 operates to deliver appropriate electrical stimulation therapy to heart 710, if the determined arrhythmia is a tachycardia, one or more of LCPs 702, 704, and 706 may deliver ATP therapy to heart 710. In examples where the determined arrhythmia is a bradycardia, one or more of LCPs 702, 704, and 706 may deliver bradycardia therapy to heart 710. In examples where the determined arrhythmia is un-synchronized contractions, one or more of LCPs 702, 704, and 706 may deliver CRT to heart 710. It is contemplated that less than all of LCPs 702, 704, and 706 may deliver electrical stimulation therapy in response to the detection of an arrhythmia. For example, only a single of LCPs 702, 704, and 706 may deliver electrical stimulation therapy. In other examples, two of LCPs 702, 704, and 706 may deliver electrical stimulation therapy.

In some embodiments, if a need for anti-tachycardia pacing therapy is determined, one of the LCPs 702, 704 may instruct the other LCP to assist in providing biventricular anti-tachycardia pacing therapy. For example, LCP 704 may provide right ventricular anti-tachycardia pacing therapy while LCP 702 remains dormant. In some embodiments, LCP 702 may provide left ventricular anti-tachycardia pacing therapy while LCP 704 remains dormant. In some embodiments, LCP 706 may be instructed to remain dormant while one or both of LCP 702 and 704 deliver pacing therapy. In some embodiments, both LCP 702 and LCP 704 may be instructed to remain dormant while another device provides pacing therapy.

In accordance with the above described description, one can see how such techniques may be extended to systems that have more than three LCP devices. For example, in a four LCP device system, any of one, two, three, or four devices may be used to determine an occurrence of an arrhythmia before the system begins to deliver appropriate electrical stimulation therapy. In some such examples, all, some, or one of the LCP devices may initially actively sense and determine the occurrences of arrhythmias. In examples where less than all are initially actively sensing, once one of the actively sensing devices determines an occurrence of an arrhythmia, and communicates that determination to other devices of the system, at least one of the other devices of the system may begin to actively sense cardiac activity and determine occurrences of arrhythmias. Again, the techniques described above may be extended to systems that include any number of LCP devices or other devices, such as five, six, seven, or any other number that is practically feasible for implantation within a patient's body.

Additionally, although described above with respect to three or more LCP devices, the same techniques may be applied to any of the systems described with respect to FIGS. 4-5. For example, any of systems 400 and 500 may further include a third device, such as a second LCP device. In such systems, the three devices may operate in accordance with any of the above described techniques of system 700, with the pulse generator capable of sensing for arrhythmias and/or delivering electrical stimulation therapy. In other examples, any of systems 400 and 500 may include a plurality of additional devices. For example, any of systems 400 and 500 may include three, four, five, or any number of LCP devices that are practical for implantation with a patient in addition to pulse generators 406 and 506. Accordingly, in such examples, the devices may operate together in accordance with any of the above described techniques.

A multiple device system may, in some cases, be capable of delivering more effective electrical stimulation therapy than a single device system. For example, before beginning to deliver electrical stimulation therapy, example systems may determine which of the devices of the system first senses a depolarization wave of the heart. In such examples, such systems may direct the device which senses the depolarization wave first to deliver the electrical stimulation therapy. This may allow such systems to deliver electrical stimulation therapy at a site closer to the origin of an arrhythmia, which may increase the effectiveness of the electrical stimulation therapy.

In the example of system 700, one of the devices of system 700 may determine an occurrence of a tachyarrhythmia, either individually or in addition to provisional determinations by other devices of system 700 in accordance with any of the techniques described above. One of the devices of system 700 (e.g. a master device) may determine to deliver ATP therapy to heart 710 or to determine to direct another device of system 700 to deliver ATP therapy. Before either delivering, or directing another device to deliver ATP therapy, one of the devices of system 700 may determine which device of system 700 first senses an intrinsic cardiac depolarization wave of heart 710. The device that senses such a depolarization wave first may then begin delivery of ATP therapy.

A multiple device system may be used to help provide discrimination between atrial arrhythmias and ventricular arrhythmias. For instance, example systems described herein may operate differently depending on whether an arrhythmia is an atrial arrhythmia or a ventricular arrhythmia in order to more effectively treat such arrhythmias.

As one illustrative example, one of the devices of system 700 may determine an occurrence of a tachyarrhythmia, either individually or in addition to provisional determinations by other devices of system 700 in accordance with any of the techniques described above. Additionally, a device of system 700 may determine whether the tachycardia is an atrial tachycardia or a ventricular tachycardia. If the tachycardia is an atrial tachycardia, one or more of the devices of system 700 may determine to not deliver electrical stimulation therapy. If the tachycardia is a ventricular tachycardia, one or more of the devices of system 700 may additionally determine whether the rate of the tachycardia is above a threshold and whether the cardiac electrical signal is a polymorphic signal. If the tachycardia rate is below the threshold and the cardiac electrical signal is not a polymorphic signal, one or more of the devices of system 700 may deliver, or direct a different device of system 700 to deliver, ATP therapy to the heart 710. If the tachycardia rate is above the threshold or the cardiac electrical signal is a polymorphic signal, one or more of the devices of system 700 may deliver, or direct a different device of system 700 to deliver, a defibrillation pulse to heart 710. Discriminating between such atrial and ventricular arrhythmias, and responding differently to the different types of arrhythmias, may increase the effectiveness of delivered electrical stimulation therapy and decrease negative outcomes of any delivered electrical stimulation therapy. The above description is just one example of how the disclosed systems may operate to discriminate between various arrhythmias and deliver electrical stimulation therapy in response to the different determined arrhythmias.

Figure 8:
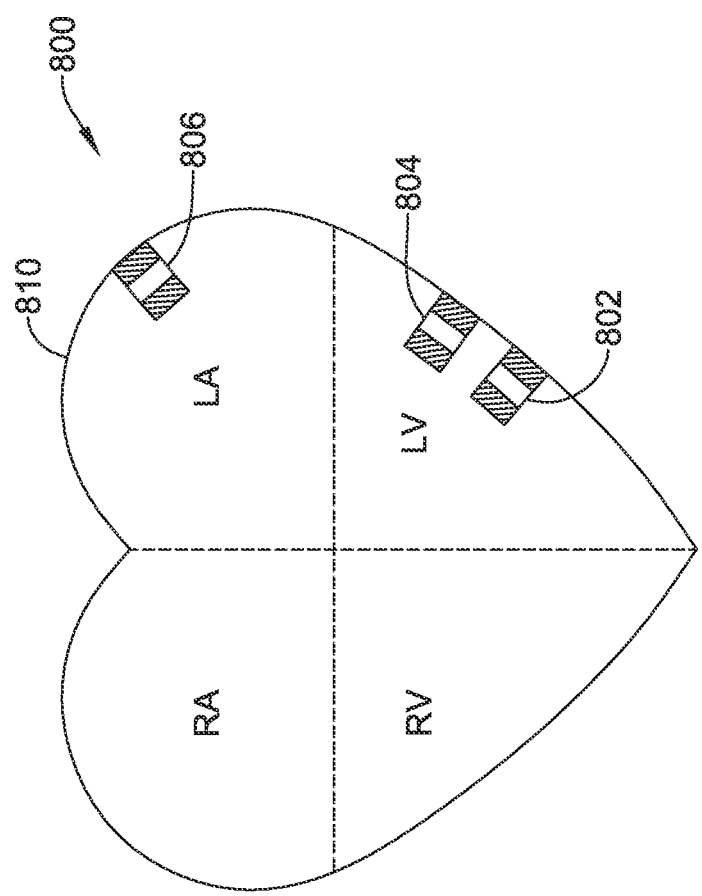
FIG. 8 is a schematic diagram illustrating a multiple leadless cardiac pacemaker (LCP) system where two LCPs are implanted within a single chamber of a heart, in accordance with yet another example of the present disclosure.
Figure 9:
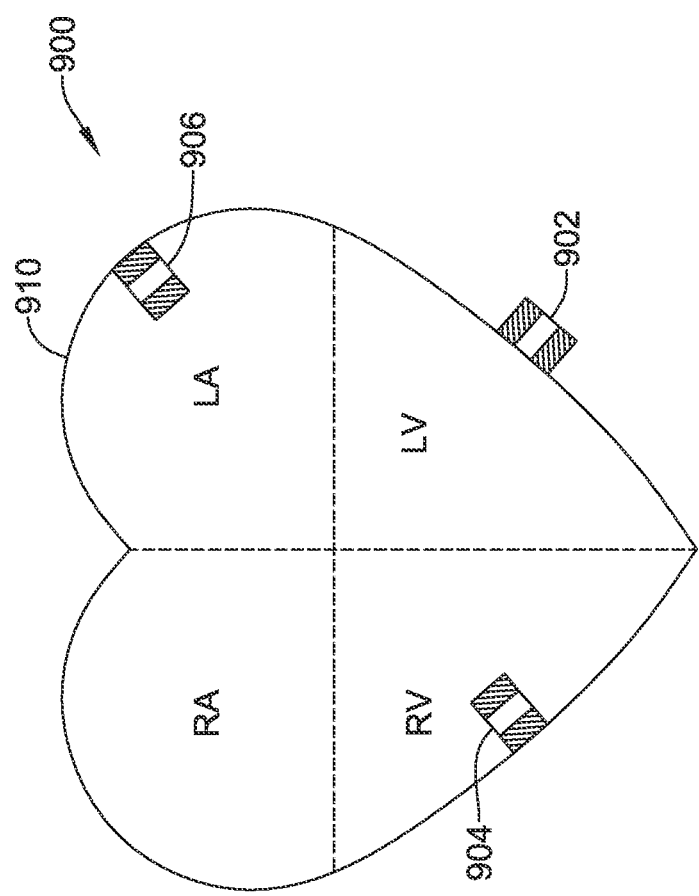
FIG. 9 is a schematic diagram illustrating a multiple leadless cardiac pacemaker (LCP) system where one of the LCPs is implanted on an epicardial surface of a heart, in accordance with another example of the present disclosure.

FIGS. 8 and 9 illustrate other example implantation locations and configurations for a multiple device medical system. For example, medical device system 800 of FIG. 8 shows three LCP devices, LCPs 802, 804, and 806. Two of the LCP devices, LCPs 802 and 804, are shown implanted within a single chamber of heart 810. In other examples, all three devices may be implanted within a single chamber of heart 810. Although two LCP's 802 and 804 are shown implanted within the LV of heart 810, in other examples, any of the chambers of heart 810 may include multiple implanted LCP devices. Implanting multiple devices within a single chamber may enhance the effectiveness of delivered electrical stimulation, as the multiple devices may increase the chances of delivering electrical stimulation therapy near a cardiac site that is an origin of an arrhythmia causing signal. As described previously with respect to the other systems, any of the other system described herein, such as systems 400 and 500 may include one or more devices implanted within a single chamber of the heart, as desired.

Medical device system 900 of FIG. 9 includes an LCP 902 implanted on an epicardial surface of heart 910. LCPs 904 and 906 are shown implanted on an endocardial surface of heart 910. In some instances, one or more additional devices of system 900 may be implanted on an epicardial surface. In some instance, a device implanted on an epicardial surface of a heart may sense intrinsic cardiac electrical signals and/or deliver appropriate electrical stimulation therapy to the heart. Accordingly, any of the systems described herein may include one or more devices implanted on an endocardial surface of a heart, as desired.

Figure 10:
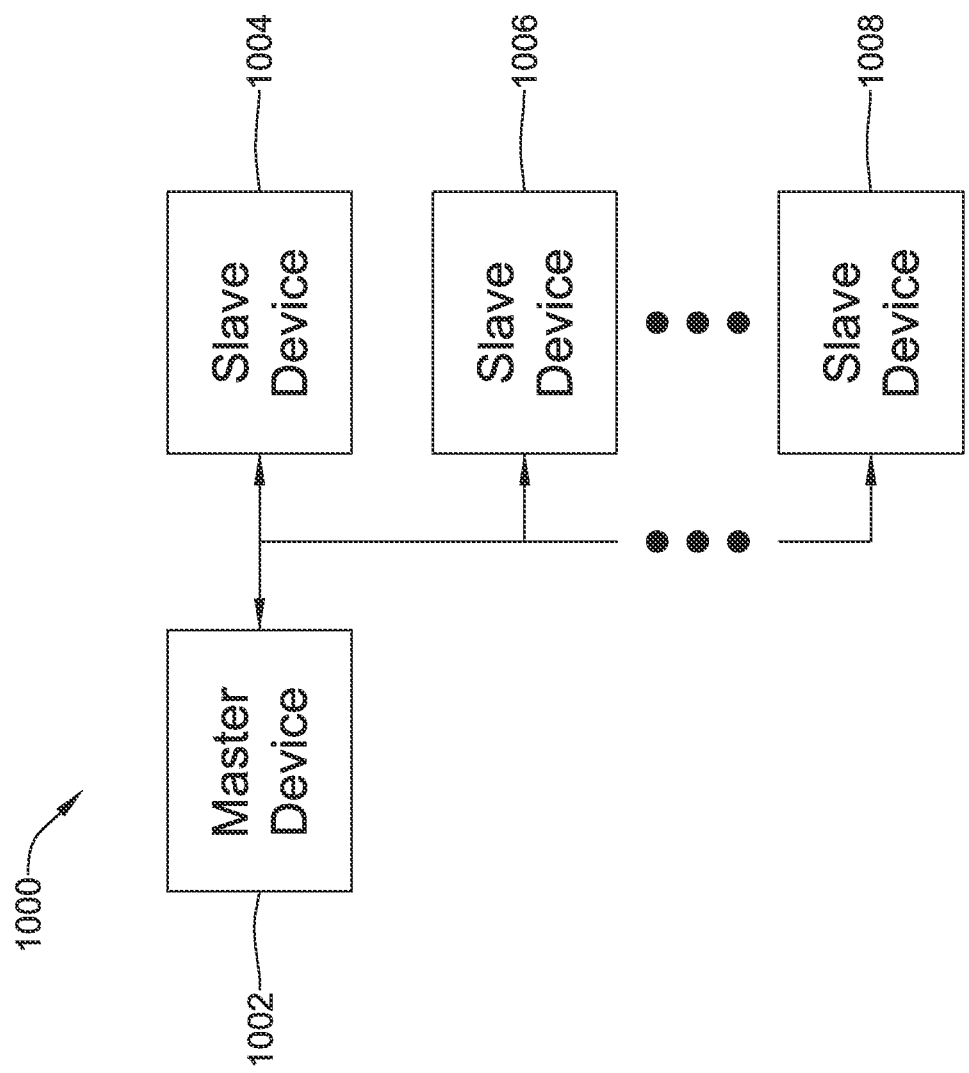
FIG. 10 is a block diagram of an exemplary medical system including a master device and multiple slave devices.

As noted above, in some embodiments, one device in a medical system may act a master device and the other devices may act as slave devices. FIG. 10 is a block diagram of an illustrative medical device system 1000 that includes a master device 1002 and multiple slave devices 1004, 1006, and 1008. In the example shown, the master device 1002 may conductively communicate with the slave devices 1004, 1006, and 1008 though the body of the patient. In other examples, the master and slave devices may communicate via a different communication mechanism, such as through radiofrequency (RF) signals, inductive coupling, optical signals, acoustic signals, or any other suitable for communication mechanism, as desired.

In one example, the master device 1002 may be an ICD device, for example, an ICD or an S-ICD, and may be configured to receive cardiac information from one or more slave devices 1004, 1006, and 1008. In some cases, the slave devices may be LCPs. The communicated cardiac information may include, for example, cardiac electrical signals sensed by the slave devices 1004, 1006, and 1008, preliminary determinations made by the slave devices 1004, 1006, and 1008, or other information sensed or determined by the slave devices 1004, 1006, and 1008. In some examples, master device 1002 may also sense cardiac activity. In such examples, master device 1002 may determine occurrences of arrhythmias based on either its own sensed cardiac activity and/or the received cardiac activity from the slave devices 1004, 1006 and 1008. In some instances, master device 1002 may determine that the cardiac activity from one or multiple devices of system 1000 indicates an occurrence of an arrhythmia. In some cases, although multiple devices of system 1000 may each be sensing cardiac activity, only a single device, such as master device 1002, may make the determination that a cardiac arrhythmia is occurring and that an appropriate electrical stimulation therapy is desired.

In response to determining an occurrence of an arrhythmia, master device 1002 may determine to deliver electrical stimulation therapy. In one example, master device 1002 may determine an appropriate electrical stimulation therapy based on the type of arrhythmia. Additionally, master device 1002 may determine which device or devices should deliver the electrical stimulation therapy. Master device 1002 may direct one or more of the devices, which might include the master device itself, to actually deliver the desired electrical stimulation therapy. Master device 1002 may operate according to any of the previously disclosed techniques. For example, master device 1002 may determine one or more provisional determinations of occurrences of arrhythmias before determining an actual occurrence of an arrhythmia. Master device 1002 may additionally distinguish between atrial and ventricular arrhythmias and determine appropriate electrical stimulation therapy to deliver based on the determined type of arrhythmia. In some examples, master device 1002 may determine which device or devices need to deliver electrical stimulation therapy based on which device or devices sensed the cardiac depolarization wave first of a cardiac cycle.

In some instances, multiple devices of system 1000 may determine occurrences of arrhythmias. For example, slave devices 1004, 1006, and 1008 may each determine occurrences of arrhythmias and may communicate such determinations to master device 1002. In some examples, such determinations may be considered actual or provisional determinations. Based on such received determinations, master device 1002 may determine an occurrence of an arrhythmia, in accordance with any of the previously disclosed techniques. Based on an determination of an arrhythmia, master device 1002 may deliver, and/or direct one or more of slave devices 1004, 1006, and 1008 to deliver, appropriate electrical stimulation therapy.

In some cases, not all of master device 1002 and slave devices 1004, 1006, and 1008 may be actively sensing for an arrhythmia. For instance, as described previously, in some examples only a single, or less than all of master device 1002 and slave devices 1004, 1006, and 1008 may be actively sensing for an arrhythmia. In at least one example, the actively sensing device may be sending cardiac activity to master device 1002. Based on the received cardiac activity, master device 1002 may determine an occurrence of an arrhythmia. After determining an occurrence of an arrhythmia, master device 1002 may direct a second device of system 1000 to begin actively sensing cardiac activity. This second device may additionally communicate sensed cardiac activity to master device 1002. Again, master device 1002 may determine an occurrence of an arrhythmia based on the received cardiac activity from the second device. After making one or more determinations of an occurrence of an arrhythmia, master device 1002 may deliver, or direct one or more of slave devices 1004, 1006, and 1008 to deliver, appropriate electrical stimulation therapy. In other examples, instead of sending sensed cardiac data, the devices may send determinations of occurrences of an arrhythmia to master device 1002. In some cases, master device 1002 may not sense cardiac activity. Rather, master device 1002 may make determinations of occurrences of cardiac arrhythmias based on received cardiac activity and/or determinations from those slave devices that are sensing cardiac activity.

In some cases, master device 1002 may be an LCP device, an external cardioverter-defibrillator, ICP, diagnostic-only device, or a neural stimulation device. In some examples, master device 1002 and the slave devices 1004, 1006, and 1008 may have similar hardware configuration; however, they may have different software installed. In some examples, the slave devices 1004, 1006, and 1008 may be set to a "slave mode" while master device 1002 may be set to a "master mode", even though all devices share the same hardware and software features. Additionally, in some examples, the devices of system 1000 may switch between being configured as a master device and a slave device. For example, an external programmer may connect to any of the devices of such systems and alter the programming of any of the devices of the system, as desired.

Figure 11:
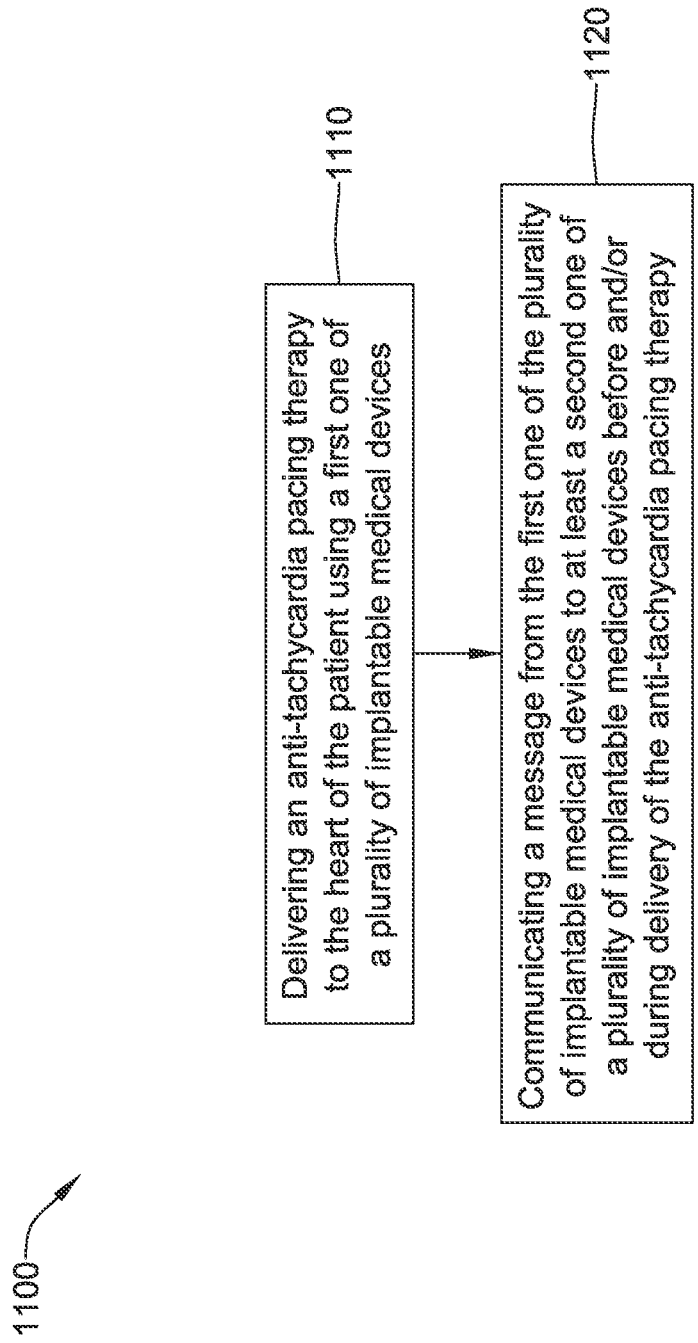
FIG. 11 is a flow diagram showing an illustrative method of the present disclosure.

FIG. 11 is a flow chart showing an illustrative method 1100 that may be carried out using a plurality of implantable medical devices. At block 1110, an anti-tachycardia pacing therapy is delivered to the heart of the patient using a first one of the plurality of implantable medical devices. In some embodiments, this step is carried out by a leadless cardiac pacemaker (LCP). In some embodiments, the anti-tachycardia pacing therapy is delivered to a ventricle of the heart.

A message is communicated from the first one of the plurality of implantable medical devices to at least a second one of the plurality of implantable medical devices before and/or during delivery of the anti-tachycardia pacing therapy, as generally indicated at block 1120. In some embodiments, the second one of the plurality of medical devices may be a leadless cardiac pacemaker (LCP), a subcutaneous implantable cardioverter-defibrillator (S-ICD), an ICD, a diagnostic only device, a neural-stimulator, or any other suitable device. In some embodiments, the second one of the plurality of implantable medical devices is configured to deliver a therapy to an atrium of the patient's heart. In some embodiments, the message delivered to the second one of the plurality of implantable medical device modifies the therapy that is delivered by the second one of the plurality of implantable devices, such as causes the second one of the plurality of implantable medical devices to assist the first implantable medical device in delivering therapy, temporarily stop providing therapy, temporary shutdown, or operate in any other suitable manner as desired.

In some embodiments, the first one of the plurality of implantable medical devices is a leadless cardiac pacemaker (LCP) that is configured to deliver anti-tachycardia pacing therapy to a first ventricle site, and the second one of the plurality of implantable medical devices is a leadless cardiac pacemaker (LCP) that is configured to deliver anti-tachycardia pacing therapy to a second ventricle site. In some embodiments, the anti-tachycardia pacing therapy that is delivered by the second one of the plurality of implantable medical devices is affected, at least in part, by the communicated message from the first one of the plurality of implantable medical devices. In some embodiments, the communicated message may cause the second one of the plurality of implantable medical devices to assist the first implantable medical device in delivering the anti-tachycardia pacing therapy, temporarily stop providing therapy, temporary shutdown, or operate in any other suitable manner as desired.

Figure 12:
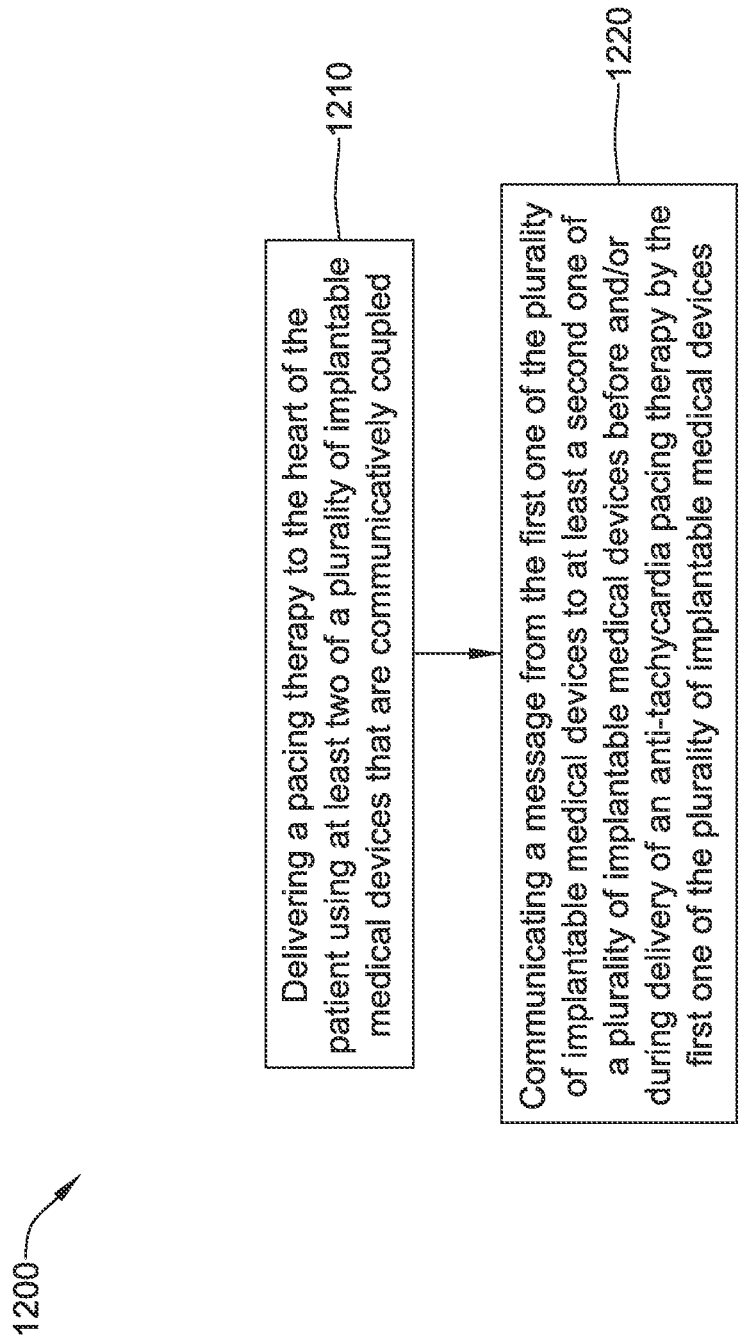
FIG. 12 is a flow diagram showing another illustrative method of the present disclosure.

FIG. 12 is a flow chart showing another illustrative method 1200 that may be carried out using a plurality of implantable medical devices. At block 1210, a pacing therapy is delivered to the heart of the patient using at least two of a plurality of implantable medical devices. The at least two implantable medical devices are communicatively coupled. If it is determined that anti-tachycardia pacing therapy is to be delivered by a first one of the plurality of implantable medical devices, a message is communicated from the first one of the plurality of implantable medical devices to at least a second one of the plurality of implantable medical devices before and/or during delivery of the anti-tachycardia pacing therapy by the first one of the plurality of implantable medical devices, as generally indicated at block 1220. The communicated message may cause the second one of the plurality of implantable medical devices to, for example, assist the first implantable medical device in delivering the anti-tachycardia pacing therapy, temporarily stop providing therapy, temporary shutdown, or operate in any other suitable manner as desired.

Figure 13:
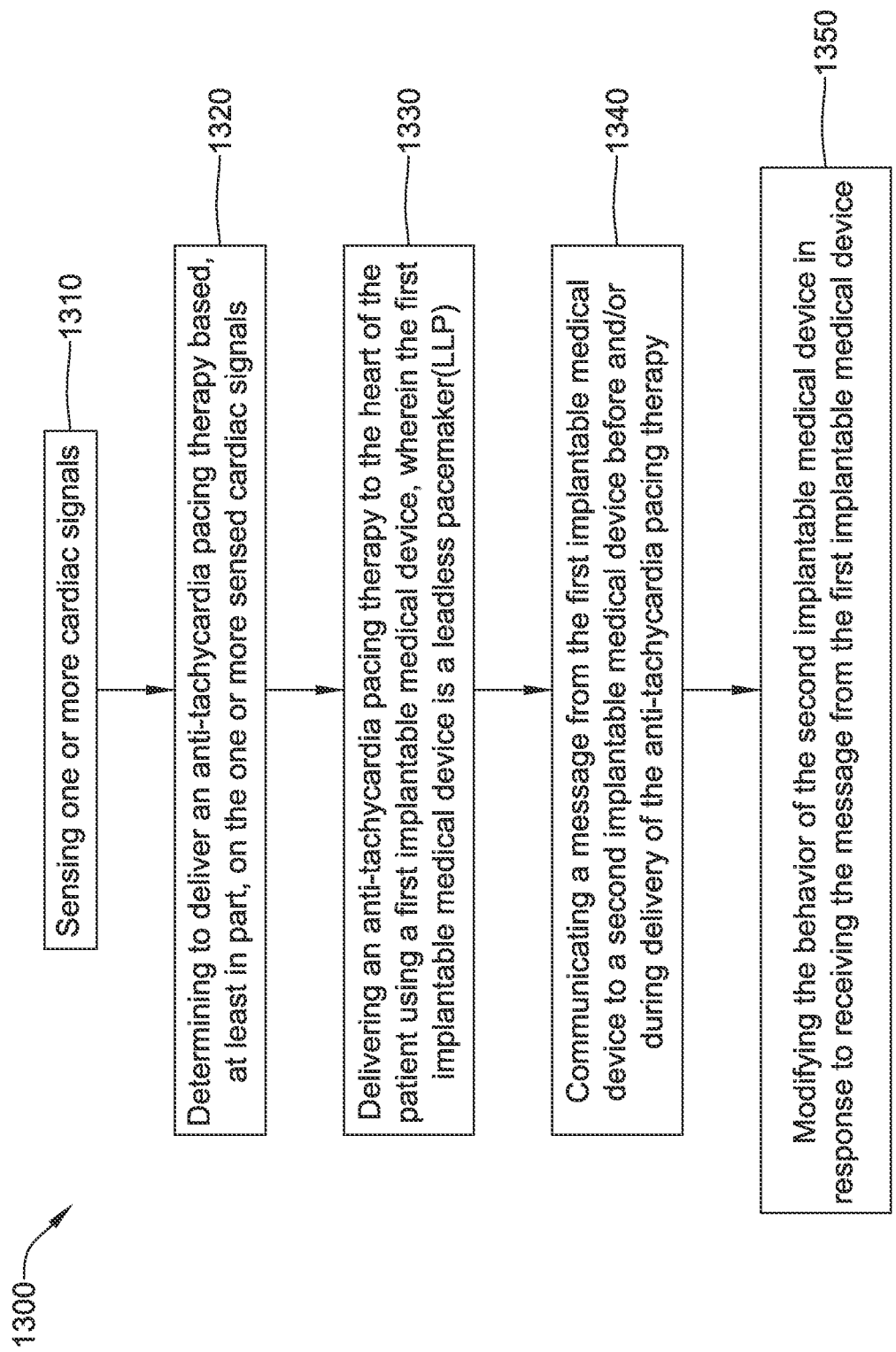
FIG. 13 is a flow diagram showing yet another illustrative method of the present disclosure.

FIG. 13 is a flow chart showing yet another illustrative method 1300 that may be carried out using a plurality of implantable medical devices. At block 1310, one or more cardiac signals may be sensed by an implanted medical device. In some embodiments, the one or more cardiac signals are sensed by a first implantable medical device. A determination is made to deliver an anti-tachycardia pacing therapy based, at least in part, on the one or more sensed cardiac signals, as generally indicated at block 1320. In some embodiments, the determination is made by the first implantable medical device. At block 1330, an anti-tachycardia pacing therapy is delivered to the heart of the patient using a first implantable medical device such as a leadless cardiac pacemaker (LCP). A message is communicated from the first implantable medical device (e.g. leadless cardiac pacemaker) to a second implantable medical device before and/or during delivery of the anti-tachycardia pacing therapy, as generally indicated at block 1340. In some embodiments, the second implantable medical device is also a leadless cardiac pacemaker (LCP). At block 1360, the behavior of the second implantable medical device is modified in response to receiving the message from the first implantable medical device. For example, the message may cause the second one of the plurality of implantable medical devices to assist the first implantable medical device in delivering the anti-tachycardia pacing therapy, temporarily stop providing therapy, temporary shutdown, or operate in any other suitable manner as desired.

In some embodiments, the therapy modified by the communicated message may be one or more of a bradycardia therapy, a resynchronization therapy, a neural stimulation therapy, a tachyarrhythmia therapy, a pacing therapy and/or a shock therapy. In some embodiments, a diagnostic feature of the second one of the plurality of medical devices may be modified by the communicated message. The diagnostic feature may be modified by one or more of modifying data storage (e.g. enabling, disabling, increasing, deceasing, suspending, deleting, copying), enabling or disabling a sensor, storing the occurrence of the communicated message, or/and storing information related to the effectiveness of the anti-tachycardia pacing.

Additional Examples

In a first example, a method for delivering anti-tachycardia pacing therapy includes delivering an anti-tachycardia pacing therapy to the heart of the patient using a first one of a plurality of implantable medical devices and communicating a message from the first one of the plurality of implantable medical devices to at least a second one of the plurality of implantable medical devices before and/or during delivery of the anti-tachycardia pacing therapy.

In addition or alternatively, and in a second example, the first one of the plurality of implantable medical devices of the first example is a leadless cardiac pacemaker (LCP).

In addition or alternatively, and in a third example, the second one of the plurality of implantable medical devices of any of the first through second examples is a leadless cardiac pacemaker (LCP).

In addition or alternatively, and in a fourth example, the second one of the plurality of implantable medical devices of any of the first through second examples is a subcutaneous implantable cardioverter-defibrillator (SICD).

In addition or alternatively, and in a fifth example, the first one of the plurality of implantable medical devices of any of the first through fourth examples is configured to deliver the anti-tachycardia pacing therapy to a ventricle of the patient's heart.

In addition or alternatively, and in a sixth example, the second one of the plurality of implantable medical devices of the fifth example is a leadless cardiac pacemaker (LCP).

In addition or alternatively, and in a seventh example, the second one of the plurality of implantable medical devices of the fifth example is configured to deliver a therapy to an atrium of the patient's heart.

In addition or alternatively, and in an eighth example, the second one of the plurality of implantable medical devices of any of the first through seventh example is configured to deliver a therapy to the patient's heart, and the message received from the first one of the plurality of implantable medical devices modifies the therapy that is delivered by the second one of the plurality of implantable medical devices.

In addition or alternatively, and in an ninth example, the first one of the plurality of implantable medical devices of any of the first through eighth example is a leadless cardiac pacemaker (LCP) that is configured to deliver anti-tachycardia pacing therapy to a first ventricle site, and the second one of the plurality of implantable medical devices is a leadless cardiac pacemaker (LCP) that is configured to deliver anti-tachycardia pacing therapy to a second ventricle site, wherein the anti-tachycardia pacing therapy that is delivered by the second one of the plurality of implantable medical devices is affected, at least in part, by the communicated message from the first one of the plurality of implantable medical devices.

In addition or alternatively, and in a tenth example, the second one of the plurality of implantable medical devices of the first example is configured to deliver a neural stimulation therapy to the patient.

In addition or alternatively, and in an eleventh example, delivering anti-tachycardia pacing therapy to the heart of the patient by at least one of the plurality of implantable medical devices of any of the first through tenth examples includes delivering anti-tachycardia pacing therapy to the heart of the patient using at least two of the plurality of implantable medical devices that are communicatively coupled.

In a twelfth example, a method for delivering anti-tachycardia pacing therapy includes sensing one or more cardiac signals, determining to deliver an anti-tachycardia pacing therapy based, at least in part, on the one or more sensed cardiac signals, delivering an anti-tachycardia pacing therapy to the heart of the patient using a first implantable medical device, wherein the first implantable medical device is a leadless cardiac pacemaker (LCP), communicating a message from the leadless cardiac pacemaker (LCP) to a second implantable medical device before and/or during delivery of the anti-tachycardia pacing therapy and modifying the behavior of the second implantable medical device in response to receiving the message from the first implantable medical device.

In addition or alternatively, and in a thirteenth example, the sensing and determining steps of the twelfth example are performed at least in part by the first implantable medical device.

In addition or alternatively, and in a fourteenth example, the second implantable medical device of any of the twelfth through thirteenth example is a leadless cardiac pacemaker (LCP).

In a fifteenth example, an implantable medical device system includes a first implantable medical device and a second implantable medical device that is communicatively coupled with the first implantable medical device. The first implantable medical device is configured to deliver anti-tachycardia pacing therapy to the heart of the patient and, before or during delivery of the anti-tachycardia pacing therapy, the first implantable medical device is configured to inform the second implantable medical device of the delivery of anti-tachycardia pacing therapy to the heart of the patient by the first implantable medical device.

In addition or alternatively, and in a sixteenth example, the first implantable medical device of the fifteenth example is a leadless cardiac pacemaker (LCP) and the second implantable medical device is a leadless cardiac pacemaker (LCP).

In addition or alternatively, and in a seventeenth example, the first implantable medical device of the fifteenth example is a leadless cardiac pacemaker (LCP) and the second implantable medical device is a subcutaneous implantable cardioverter-defibrillator (SICD).

In addition or alternatively, and in an eighteenth example, the first implantable medical device of the fifteenth example is a leadless cardiac pacemaker (LCP) and the second implantable medical device is a neural stimulation device.

In addition or alternatively, and in an nineteenth example, the second implantable medical device of any of the fifteenth through eighteenth examples is configured to be inhibited in response to being informed of an delivery of anti-tachycardia pacing therapy to the heart of the patient by the first implantable medical device.

In addition or alternatively, and in a twentieth example, one or more electrodes of the second implantable medical device of the nineteenth example are rendered inactive when the second implantable medical device is inhibited.

Those skilled in the art will recognize that the present disclosure may be manifested in a variety of forms other than the specific embodiments described and contemplated herein. As one example, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A method for delivering anti-tachycardia pacing therapy to a heart of a patient, the method comprising:
   determining, by a first leadless cardiac pacemaker (LCP), to deliver an anti-tachycardia pacing therapy;
   delivering the anti-tachycardia pacing therapy to the heart of the patient using the first LCP; and
   in response to having determined to proceed with delivering an anti-tachycardia pacing therapy, communicating a message via sub-threshold, non-capture, conducted communication pulses from the first LCP to at least a second leadless cardiac pacemaker (LCP) before delivery of the anti-tachycardia pacing therapy by the first LCP such that the second LCP modifies its behavior in response to receiving the message from the first LCP.

2. The method of claim 1, wherein the first LCP is configured to deliver the anti-tachycardia pacing therapy to a ventricle of the patient's heart.

3. The method of claim 2, wherein the second LCP is configured to deliver a therapy to an atrium of the patient's heart.

4. The method of claim 1, wherein the second LCP is configured to deliver a therapy to the patient's heart, and the message received from the first LCP modifies the therapy that is delivered by the second LCP.

5. The method of claim 1, wherein the first LCP is configured to deliver anti-tachycardia pacing therapy to a first ventricle site, and the second LCP is configured to deliver anti-tachycardia pacing therapy to a second ventricle site, wherein the anti-tachycardia pacing therapy that is delivered by the second LCP is affected, at least in part, by the communicated message from the first LCP.

6. The method of claim 1, wherein delivering anti-tachycardia pacing therapy to the heart of the patient comprises:
   delivering anti-tachycardia pacing therapy to the heart of the patient using at least the first LCP and the second LCP,
   wherein at least the first LCP and the second LCP s are communicatively coupled.

7. A method for delivering anti-tachycardia pacing therapy to a heart of a patient, the method comprising:
   sensing one or more cardiac signals;
   determining to deliver an anti-tachycardia pacing therapy based, at least in part, on the one or more sensed cardiac signals;
   delivering an anti-tachycardia pacing therapy to the heart of the patient using a first leadless cardiac pacemaker (LCP);
   in response to having determined to proceed with delivering an anti-tachycardia pacing therapy, communicating a message via non-capture communication pulses from the first LCP to a second leadless cardiac pacemaker (LCP) before delivery of the anti-tachycardia pacing therapy; and
   modifying the behavior of the second LCP in response to receiving the message via the non-capture communication pulses from the first LCP.

8. The method of claim 7, wherein the sensing and determining steps are performed at least in part by the first LCP.

* * * * *